(12) United States Patent
Hoser

(10) Patent No.: US 9,657,340 B2
(45) Date of Patent: May 23, 2017

(54) ISOTHERMAL NUCLEIC ACID AMPLIFICATION

(71) Applicant: ORION PHARMA (UK) LIMITED, London (GB)

(72) Inventor: Mark Jay Hoser, Broadstairs (GB)

(73) Assignee: ORION PHARMA (UK) LIMITED, London (GB)

( * ) Notice: Subject to any disclaimer, the term of this patent is extended or adjusted under 35 U.S.C. 154(b) by 171 days.

(21) Appl. No.: 14/709,793

(22) Filed: May 12, 2015

(65) Prior Publication Data

US 2015/0307928 A1    Oct. 29, 2015

Related U.S. Application Data

(62) Division of application No. 12/997,382, filed as application No. PCT/GB2009/050662 on Jun. 11, 2009, now Pat. No. 9,062,344.

(30) Foreign Application Priority Data

Jun. 11, 2008 (GB) .................................. 0810650.2
Dec. 11, 2008 (GB) .................................. 0822533.6

(51) Int. Cl.
     *C12Q 1/68*          (2006.01)

(52) U.S. Cl.
     CPC ................................ *C12Q 1/6844* (2013.01)

(58) Field of Classification Search
None
See application file for complete search history.

(56) References Cited

U.S. PATENT DOCUMENTS

| 6,432,642 B1 | 8/2002 | Livak et al. |
| 6,596,486 B2 | 7/2003 | Frank-Kamenetskii et al. |
| 2005/0112631 A1 | 5/2005 | Piepenburg et al. |
| 2007/0054296 A1 * | 3/2007 | Piepenburg .......... C12Q 1/6816 435/6.13 |
| 2011/0123991 A1 | 5/2011 | Hoser |

FOREIGN PATENT DOCUMENTS

| JP | 2006271372 A | 12/2006 |
| WO | 0055353 A1 | 9/2000 |
| WO | 01/20035 | 3/2001 |
| WO | 0114566 A2 | 3/2001 |
| WO | 2005118853 A2 | 12/2005 |
| WO | 2006/051988 | 5/2006 |
| WO | WO 2006087574 A2 * | 8/2006 ............. C12Q 1/682 |
| WO | 2007/096702 | 8/2007 |
| WO | 2008/035205 | 3/2008 |

OTHER PUBLICATIONS

Bleuit et al., Mediator proteins orchestrate enzyme-ssDNA assembly during T4 recombination-dependent DNA replication and repair, PNAS, Jul. 17, 2001, vol. 98 No. 15, 8298-8305.*
International Search Report for PCT/GB2009/050662 dated Aug. 11, 2009.
Gill Pooria et al: "Nucleic acid isothermal amplification technologies—A review," Nucleosides, Nucleotides and Nucleic Acids, Taylor & Francis, Philadelphia, PA, vol. 27, No. 3, Mar. 1, 2008, pp. 224-243.
Mori Yasuyoshi et al: "Loop-mediated isothermal amplification (LAMP): a rapid, accurate, and cost-effective diagnostic method for infectious diseases," Journal of Infection and Chemotherapy, vol. 15, No. 2, Apr. 2009, pp. 62-69.
IPRP and Written Opinion of the International Searching Authority for the instant application, mailed Dec. 23, 2010.
European Search Report for EP 13178545.3 mailed Sep. 17, 2013.
Demidov (PD-loop technology; PNA openers at work, Expert Rev. Mol. Diagn. 1(3), 343-351 (2001)).
Demidov & Frank-Kamenetskii (PNA Openers and Their Applications, in Methods in Molecular Biology, vol. 208: Peptide Nucleic Acids: Methods and Protocols, 2002, pp. 119-130).
Piepenburg et al. (DNA Detection Using Recombination Proteins, PLoS Biology, vol. 4, issue 7, pp. 1115-1121 (Jul. 2006)).
Hoser, et al., Strand Invasion Based Amplification (SIBA®): A Novel Isothermal DNA Amplification Technology Demonstrating High Specificity and Sensitivity for a Single Molecule of Target Analyte, PLOS One, Nov. 24, 2014.

* cited by examiner

*Primary Examiner* — Aaron Priest
(74) *Attorney, Agent, or Firm* — Heslin Rothenberg Farley & Mesiti PC

(57) ABSTRACT

A kit for performing isothermal amplification of a nucleic acid target molecule, where the amplification relies on an upstream primer, a downstream primer, a strand invasion system and an oligonucleotide, wherein the upstream and downstream primers are not substrates for the strand invasion system during the amplification process and do not amplify the target molecule independently of the strand invasion system, wherein the oligonucleotide is a substrate for the strand invasion system.

15 Claims, 13 Drawing Sheets

US 9,657,340 B2

ISOTHERMAL NUCLEIC ACID AMPLIFICATION

CROSS REFERENCE TO RELATED APPLICATIONS

This application is a divisional of U.S. patent application Ser. No. 12/997,382, which was filed on Dec. 10, 2010, as a National Phase filing under 35 U.S.C. §371 of International Patent Application No. PCT/GB2009/050662 filed on Jun. 11, 2009, which claims priority to: (1) GB patent application no. 0810650.2 filed on Jun. 11, 2008; and (2) GB patent application no. 0822533.6 filed on Dec. 11, 2008. The entire disclosures of each of the prior applications are hereby incorporated herein by reference.

REFERENCE TO A SEQUENCE LISTING

This application contains a sequence listing, provided as a paper copy, as required under 37 C.F.R. §1.821(c), and is herein incorporated by reference in its entirety, as required under 37 C.F.R. §1.52(e)(5). A copy of the sequence listing is also provided under 37 C.F.R. §1.821(e), as a computer readable form.

FIELD OF THE INVENTION

The invention relates to the amplification of nucleic acids, in particular to an isothermal process for amplifying a double-stranded nucleic acid target molecule.

BACKGROUND OF THE INVENTION

Within nucleic acid and genetic material technologies, it is often necessary to determine whether a gene, a part of a gene, or a nucleotide sequence is present in a living organism, a cellular extract of this organism, or a biological sample. Since any gene or part of a gene is characterized by a specific sequence of nucleotide bases, it is only necessary to search directly for the presence of all or part of said specific sequence in a sample containing a mixture of polynucleotides.

There is enormous interest in this search for specific polynucleotide sequences, particularly in detection of pathogenic organisms, determination of the presence of alleles, detection of the presence of lesions in a host genome, or detection of the presence of a particular RNA or modification of a cell host. Genetic diseases such as Huntington's disease, Duchenne's disease, phenylketonuria, and beta thalassemia can thus be diagnosed by analyzing nucleic acids from the individual. Also it is possible to diagnose or identify viruses, viroids, bacteria, fungi, protozoans, or any other form of plant or animal life by tests employing nucleic probes.

Once the specific sequence of an organism or a disease is known, the nucleic acids should be extracted from a sample and a determination should be made as to whether this sequence is present. Various methods of nucleic acid detection have been described in the literature. These methods are based on the properties of purine-pyrimidine pairing of complementary nucleic acid strands in DNA-DNA, DNA-RNA, and RNA-RNA duplexes.

This pairing process is effected by establishing hydrogen bonds between the adenine-thymine (A-T) and guanine-cytosine (G-C) bases of double-stranded DNA; adenine-uracil (A-U) base pairs can also form by hydrogen bonding in DNA-RNA or RNA-RNA duplexes. The pairing of nucleic acid strands for determining the presence or absence of a given nucleic acid molecule is commonly called "nucleic acid hybridization" or simply "hybridization".

The most direct method for detecting the presence of a target sequence in a nucleic acid sample is to obtain a "probe" whose sequence is sufficiently complementary to part of the target nucleic acid to hybridize therewith. A pre-synthesised probe can be applied in a sample containing nucleic acids. If the target sequence is present, the probe will form a hybridization product with the target. In the absence of a target sequence, no hybridization product will form. Probe hybridization may be detected by numerous methods known in the art. Commonly the probe may be conjugated to a detectable marker. Fluorescent or enzymatic markers form the basis of molecular beacons, Taqman and other cleavable probes in homogeneous systems. Alternatively the probe may be used to capture amplified material or labelled such that the amplicon is detected after separating a probe hybridized to the amplicon from non-hybridized material.

The main difficulty in this approach, however, is that it is not directly applicable to cases where the number of copies of the target sequence present in a sample is small, less than approximately $10^7$ copies. Under these conditions it is difficult to distinguish specific attachment of a probe to its target sequence from non-specific attachment of the probe to a sequence different from the target sequence. One of the solutions to this problem is to use an amplification technique which consists of augmenting the detection signal by a preliminary technique designed to specifically and considerably increase the number of copies of a target nucleic acid fragment if it is present in the sample.

The articles by Lewis (1992, Genetic Engineering News 12: 1-9) and Abramson and Myers (1993, Curr. Opin. Biotechnol. 4: 41-47) are good general surveys of amplification techniques. The techniques are based mainly on either those that require multiple cycles during the amplification process or those that are performed at a single temperature.

Cycling techniques are exemplified by methods requiring thermo-cycling and the most widely used of this class of technology is PCR (polymerase chain reaction, U.S. Pat. Nos. 4,683,195, 4,683,202, and 4,800,159; European Patent No. 0 201 184) which enables the amplification of a region of interest from a DNA or RNA. The method usually consists of three steps:
(i) dissociating (denaturing) a double-stranded DNA into single-stranded DNAs by heat denaturation/melting (FIG. 1, B);
(ii) annealing a primer oligonucleotide to the single-stranded DNA (FIG. 1, B); and
(iii) synthesizing (extending) a complementary strand from the primer in order to copy a region of a DNA of interest (FIG. 1, C).

After this process is completed the system is heated which separates the complementary strands and the process is repeated. Typically 20-40 cycles are performed to amplify genomic DNA to the extent that it can be further analysed.

The majority of exponential nucleic acid amplification processes rely on an excess of upstream and downstream primers that bind to the extreme 3' terminus and the complement of the extreme 5' end of the target nucleic acid template under investigation as shown in FIG. 1, A-C.

A second class of amplification techniques, known as isothermal techniques, are those that are performed at a single temperature or where the major aspect of the amplification process is performed at a single temperature. In contrast to the PCR process where the product of the reaction is heated to separate the two strands such that a further primer can bind to the template repeating the process, the isothermal techniques rely on a strand displacing polymerase in order to separate/displace the two strands of the duplex and re-copy the template. This well-known property has been the subject of numerous scientific articles (see for example Y. Masamute and C. C. Richardson, 1971, J. Biol. Chem. 246, 2692-2701; R. L. Lechner et al., 1983, J. Biol Chem. 258, 11174-11184; or R. C. Lundquist and B. M. Olivera, 1982, Cell 31, 53-60). The key feature that differentiates the isothermal techniques is the method that is applied in order to initiate the reiterative process.

Broadly isothermal techniques can be subdivided into those methods that rely on the replacement of a primer to initiate the reiterative template copying (exemplified by HDA (Helicase Dependent Amplification), exonuclease dependent amplification (EP1866434), Recombinase Polymerase Amplification (RPA) and Loop Mediated Amplification (LAMP)) and those that rely on continued re-use or de novo synthesis of a single primer molecule (exemplified by SDA (Strand Displacement Amplification and nucleic acid based amplification (NASBA and TMA)).

Recombinase Polymerase Amplification (RPA) is a process in which recombinase-mediated targeting of oligonucleotides to DNA targets is coupled to DNA synthesis by a polymerase (Morrical S W et. Al. J Biol Chem. 1991 Jul. 25; 266(21):14031-8 and Armes and Stemple, U.S. application Ser. No. 10/371,641). WO 2008/035205 describes an RPA process of amplification of a double stranded target nucleic acid molecule, comprising the steps of: (a) contacting UvsX, UvsY, and gp32 proteins with a first and a second single stranded nucleic acid primer specific for said double stranded target nucleic acid molecule to form a first and a second nucleoprotein primer; (b) contacting the first nucleoprotein primer to said double stranded target nucleic acid molecule to create a first D loop structure at a first portion of said double stranded target nucleic acid molecule and contacting the second nucleoprotein primer to said double stranded target nucleic acid molecule to create a second D loop structure at a second portion of said double stranded target nucleic acid molecule such that the 3' ends of said first nucleic acid primer and said second nucleic acid primer are oriented toward each other on the same double stranded target nucleic acid molecule without completely denaturing the target nucleic acid molecule; (c) extending the 3' end of said first and second nucleoprotein primers with one or more polymerases capable of strand displacement synthesis and dNTPs to generate a first and second double stranded target nucleic acid molecule and a first and second displaced strand of nucleic acid; and (d) continuing the reaction through repetition of (b) and (c) until a desired degree of amplification is reached.

In order to discriminate amplification of the target from that of futile amplification producing artefacts, probe based systems may be used that detect sequences of the amplicon under investigation that are not present in the primers supplied to the system.

All of these processes rely only on a template that comprises a binding site for the two primers at their extreme termini. A template with these qualities can be produced by non-specific interactions between the upstream and downstream primers alone and the product (primer-dimers) may be capable of efficient amplification independently of the template under investigation, as shown in FIG. 1, D-E. As a consequence of this futile amplification, the assay components become consumed by non-productive events limiting the sensitivity of the assay process.

It is an object of the present invention to provide an alternative isothermal nucleic acid amplification technique. It is a further object of the present invention to provide an exponential amplification technique. It is a further object to minimize or eliminate amplification artefacts and so provide a method for amplifying nucleic acids with increased specificity and/or sensitivity.

SUMMARY OF THE INVENTION

The present invention thus provides an isothermal process for amplifying a nucleic acid target molecule that relies on an upstream primer, a downstream primer, a strand invasion system and an oligonucleotide, wherein the upstream and downstream primers are not substrates for the strand invasion system during the amplification process and do not amplify the target molecule independently of the strand invasion system, wherein the oligonucleotide is a substrate for the strand invasion system.

In one embodiment the invention provides an isothermal process comprising the following steps:
(a) providing an upstream primer, a downstream primer, a strand invasion system and an oligonucleotide, wherein the upstream and downstream primers are not substrates for the strand invasion system during the amplification process and do not amplify the target molecule independently of the strand invasion system, wherein the oligonucleotide is a substrate for the strand invasion system;
(b) applying the oligonucleotide to the target molecule and allowing it to invade the duplex thereby rendering some or all of the target molecule single-stranded;
(c) applying the upstream primer to the single-stranded region of the target molecule and extending the 3' end of the upstream primer with polymerase and dNTPs to produce a double-stranded nucleic acid target molecule;
(d) applying the downstream primer to the single-stranded target molecule and extending the 3' end of the downstream primer with polymerase and dNTPs to produce a further double-stranded nucleic acid target molecule;
(e) continuing the reaction through repetition of (b) to (d).

In another embodiment the invention provides an isothermal process comprising the following steps:
(a) providing:
  (i) upstream and downstream primers, each comprising a single-stranded DNA molecule of less than 30 nucleotides, at least a portion of which is complementary to sequence of the target molecule;
  (ii) an oligonucleotide comprising a single-stranded DNA molecule of at least 30 nucleotides, at least a portion of which is complementary to sequence of the target molecule intervening the forward and reverse primers, and optionally further comprising a downstream element at its 3' terminus which is complementary to sequence of the target molecule and which is not a polymerase substrate;
(b) contacting the oligonucleotide (ii) with recombinase to enable it to invade the complementary region of the target molecule thereby rendering the complementary region of the target molecule and adjacent regions single-stranded;
(c) applying the upstream primer to the single-stranded region of the target molecule and extending the 3' end of the upstream primer with polymerase and dNTPs to produce a double-stranded nucleic acid target molecule;
(d) applying the downstream primer to the single-stranded target molecule and extending the 3' end of the downstream primer with polymerase and dNTPs to produce a further double-stranded nucleic acid target molecule;

(e) continuing the reaction through repetition of (b) to (d).

Advantageously these methods provide isothermal and exponential amplification of a target nucleic acid molecule. The amplification methods are more specific and sensitive than known methods and result in minimal or no amplification artefacts.

Preferably the strand invasion system comprises a recombinase system, such as the T4 UvsX/gp32/UvsY system. Preferably at least a portion of the oligonucleotide is complementary to a portion of the target sequence intervening the upstream and downstream primers. Preferably the oligonucleotide comprises a single-stranded DNA molecule of at least 30 nucleotides which may have a non-extendable 3' terminus.

Preferably the substrate for the strand invasion system facilitates the separation of the target template duplex or the product of primer extension onto the target nucleic acid. One or more additional oligonucleotides may facilitate the separation of the target duplex by the intervening oligonucleotide. Preferably the oligonucleotide comprises a downstream element at its 3' terminus which is complementary to the target sequence and which is not an efficient polymerase substrate. This may bind to the target strand released by the oligonucleotide and branch migrate into the proximal duplex nucleic acid further separating the duplex strands.

In another embodiment the invention provides a kit for isothermally amplifying a nucleic acid target molecule comprising an upstream primer, a downstream primer, a strand invasion system and an oligonucleotide, wherein the upstream and downstream primers are not substrates for the strand invasion system during the amplification process and do not amplify the target molecule independently of the strand invasion system, wherein the oligonucleotide is a substrate for the strand invasion system

DETAILED DESCRIPTION OF THE INVENTION

Figure 1:
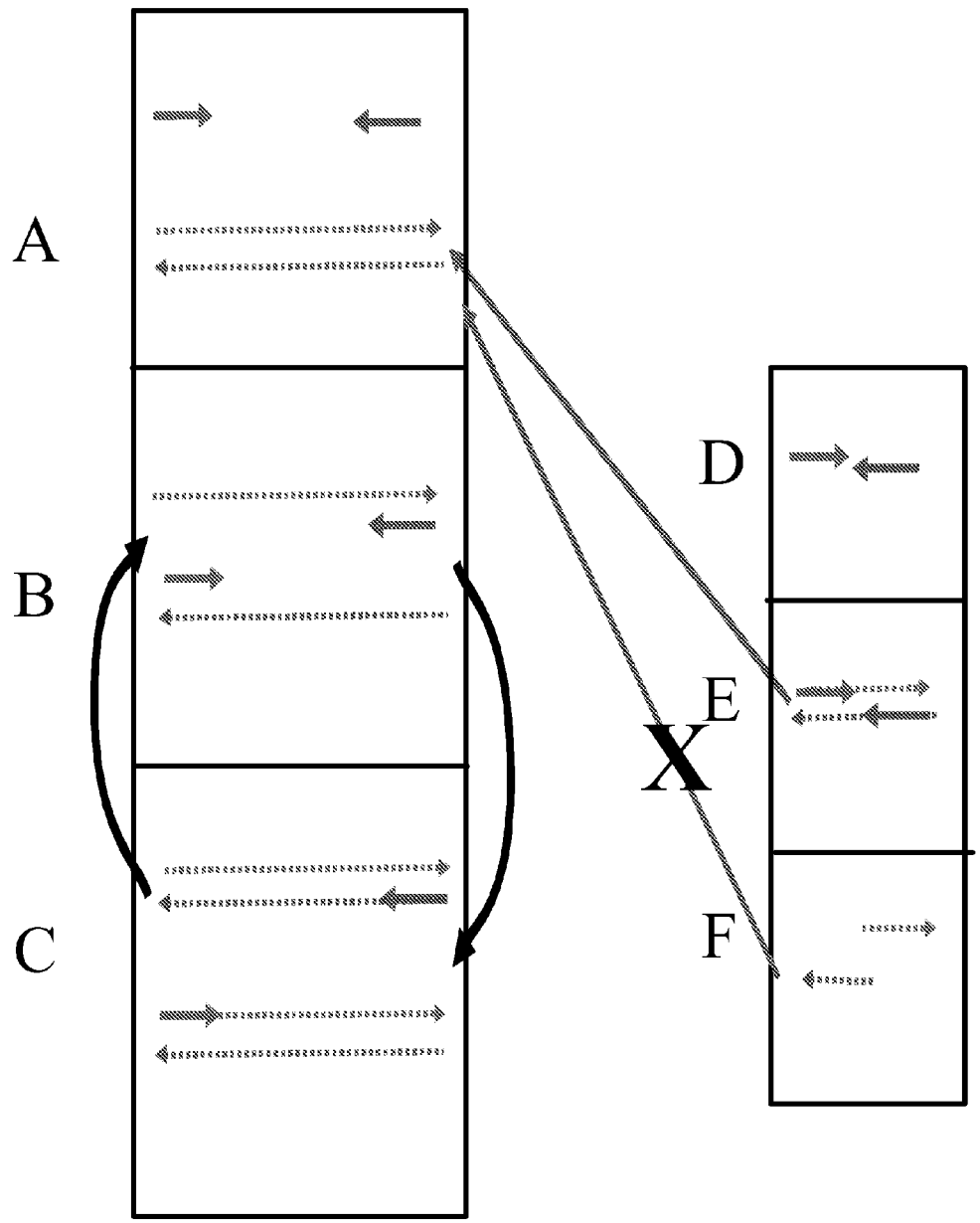
FIG. 1 shows the formation of primer dimers in a primer dependent amplification reaction.
  A: Upstream and downstream primers are incubated with a duplex template. The template is cognate at its extreme ends to the primers. One strand of the template is cognate to the upstream primer and the other strand is cognate to the downstream primer.
  B: The template strands are separated which allows the upstream and downstream primer to bind.
  C: Extension of the template bound primers produce two identical duplexes. Each duplex may participate in the previous steps in the reaction such that the template is exponentially amplified.
  1D-1F: The upstream and downstream primer copy onto each other in the absence of template. These may replace the template under investigation and can also be exponentially amplified causing an artefact.

The invention describes a method that enables isothermal and exponential amplification of a target nucleic acid. The nucleic acid sequence may comprise DNA, reverse transcribed RNA (cDNA) or genomic DNA. The nucleic acid may also contain modified or unnatural nucleosides where they can be copied by the action of a polymerase.

In contrast to other nucleic acid amplification processes, the upstream and downstream primers that bind to the extreme termini of the nucleic acid (terminal primers) are, alone, not able to induce exponential amplification of the target nucleic acid. The exponential aspect of the amplification is enabled by one or more oligonucleotides (intermediate or intervening oligonucleotides, IO) that are cognate to a proportion of the template sequence intervening the upstream and downstream primers. Since a template cognate to the upstream and downstream primers alone is not a viable amplification unit, the system can be designed such that it is impervious to loss of sensitivity by the primer dimer artefacts described in FIG. 1 and also other mispriming artefacts.

The primers are not able to amplify in the absence of the IO sequence and preferably the IO is non-extendable. As a result artefactual amplification is abolished or significantly reduced since the IO cannot impart artefactual amplification in its own right. Furthermore in some aspects of the invention, the IO comprises sequences that are not substrates for a polymerase and as such there are no artefactual events that can reproduce the amplifiable sequence in the absence of the target under investigation.

In one aspect the invention provides an isothermal process for amplifying a nucleic acid target molecule that relies on an upstream primer, a downstream primer, a strand invasion system and an oligonucleotide, wherein the upstream and downstream primers are not substrates for the strand invasion system during the amplification process and do not amplify the target molecule independently of the strand invasion system, wherein the oligonucleotide is a substrate for the strand invasion system.

In a further embodiment the invention provides an isothermal process for amplifying a double-stranded nucleic acid target molecule comprising the following steps:
(a) providing an upstream primer, a downstream primer, a strand invasion system and an oligonucleotide, wherein the upstream and downstream primers are not substrates for the strand invasion system during the amplification process and do not amplify the target molecule independently of the strand invasion system, wherein the oligonucleotide is a substrate for the strand invasion system;
(b) applying the oligonucleotide to the target molecule and allowing it to invade the duplex thereby rendering some or all of the target molecule single-stranded;
(c) applying the upstream primer to the single-stranded region of the target molecule and extending the 3' end of the upstream primer with polymerase and dNTPs to produce a double-stranded nucleic acid target molecule;
(d) applying the downstream primer to the single-stranded target molecule and extending the 3' end of the downstream primer with polymerase and dNTPs to produce a further double-stranded nucleic acid target molecule;
(e) continuing the reaction through repetition of (b) to (d).

A preferred isothermal process for amplifying a double-stranded nucleic acid target molecule comprises the following steps:
(a) providing:
  (i) upstream and downstream primers, each comprising a single-stranded DNA molecule of less than 30 nucleotides, at least a portion of which is complementary to sequence of the target molecule;
  (ii) an oligonucleotide comprising a non-extendable, single-stranded DNA molecule of at least 30 nucleotides, at least a portion of which is complementary to sequence of the target molecule intervening the forward and reverse primers;
(b) contacting the oligonucleotide (ii) with recombinase to enable it to invade the complementary region of the target molecule thereby rendering the complementary region of the target molecule and adjacent regions single-stranded;
(c) applying the upstream primer to the single-stranded region of the target molecule and extending the 3' end of the upstream primer with polymerase and dNTPs to produce a double-stranded nucleic acid target molecule;
(d) applying the downstream primer to the single-stranded target molecule and extending the 3' end of the downstream primer with polymerase and dNTPs to produce a further double-stranded nucleic acid target molecule;
(e) continuing the reaction through repetition of (b) to (d).

The inventive methods rely on the following components.

Upstream primer (or forward primer) binds to one strand of the target nucleic acid molecule at or proximal to the 5' region of the intervening oligonucleotide (IO).

Downstream primer (or reverse primer) binds to one strand of the target nucleic acid molecule at or proximal to the 3' terminus of the IO. It binds to the opposite strand to which the upstream primer binds.

Essentially, a primer binds to a template and is extended by the action of a polymerase. The forward and reverse primers must be efficient polymerase substrates. In some aspects, when used in conjunction with a recombinase system, the primers should not be competent recombinase substrates. This means that they should be less than 30 nucleotides in length. Preferably the primer is less than 25 nucleotides. Most preferably the primer is approximately 15 to 23 nucleotides. The primers are capable of binding to opposite strands of the target nucleic acid molecule. It is not essential that the entire primer binds to (is complementary with) the target sequence.

Intervening or intermediate oligonucleotide (IO) is a substrate for the strand invasion system (SIS). The substrate for the strand invasion system facilitates the separation of the target template duplex or the product of primer extension onto the target nucleic acid, thereby allowing the primers access to bind to complementary single stranded DNA on the target molecule.

In one embodiment the IO may comprise Peptide Nucleic Acid (PNA) which is able to invade double stranded DNA molecules without recourse to a recombinase. In this embodiment the PNA fulfils the role of both the oligonucleotide and the strand invading system.

In a preferred embodiment the strand invasion system comprises a recombinase system. In this embodiment at least a portion of the oligonucleotide should be complementary to a portion of the target sequence intervening the upstream and downstream primers. The intervening oligonucleotide should comprise a region that is a recombinase substrate. As recombinases preferentially effect a substrate oligonucleotide that is more than about 30 nucleotides (Formosa T. and Alberts B., JBC, (261) 6107-6118, 1986; Gamper B et al., Biochemistry, (42) 2643-2655, 2003), preferably the oligonucleotide comprises a single-stranded DNA molecule of at least about 30 nucleotides or a DNA sequence and a modified sequence that are together more than 30 nucleotide bases. Further, it should preferably have a cognate area long enough to invade a template efficiently and so at least a portion of the IO should be complementary to the target sequence intervening the forward and reverse primers. Generally this is a minimum of 24 bases and optimally around 38 bases. The 5' portion of the complementary sequence is preferably close enough to the duplex terminus that the melting temperature of the residual duplex results in dissociation of the residual duplex after binding. Usually this means that the 5' terminus of the complementary sequence should be no more than 15-20 nucleotides from the duplex terminus.

The IO may also comprise a 5' terminus that is not cognate to the template in order to efficiently seed the cognate area with recombinase. Typically this would be in excess of 12 bases. Thus the total length of the IO is preferably at least 36 bases, more preferably at least 50 bases, including the cognate region. It may also comprise a 3' terminus that is not cognate to the template.

It is preferred that the IO has a non-extendable 3' terminus. This may be achieved by incorporating one or more of several modified nucleotides. Typically these will incorporate a 3' modification of the terminal nucleotide. Examples of these modified nucleotides are dideoxynucleotide nucleotides, 3' amino-allyl, 3'-carbon spacers of various lengths, nucleotides incorporated in a reversed orientation (3'-3' linkage), 3' phosphate, 3'biotin, 3' salyl, 3'-thiol. Alternatively the terminus may comprise nucleotides incompatible with extension by a polymerase due to their poor substrate capability such as PNA or LNA or 2'-5'-linked DNA or 2'-O-methyl RNA.

Recombinase Systems

As mentioned above, preferably the strand invasion system comprises a recombinase system. Recombinases should bind to DNA molecules longer than about 30 nucleotides. Preferably, they have a strong preference for single-stranded DNA and a relatively weaker preference for double-stranded DNA. In the inventive method this allows them to bind to the IO but not to the upstream or downstream primers.

Various recombinase systems are known to those familiar with the art and have been variously reviewed (e.g. Piero R. Bianco et al. Frontiers in Bioscience 3, d570-603, 1998, 570 DNA Strand Exchange Proteins: A Biochemical and Physical Comparison). Any recombinase system may be used in the method of the invention and the detailed application of recombinases for the invasion of nucleic acid duplexes is known to those familiar with the art (Kodadek T et. Al., JBC 264, 1989; and Liu J, JBC Na Qian1, 281, 26308-26319, 2006).

The recombinase system may comprise a components derived from yeast, bacteria phage or mammals or other eukaryotes. The recombinase system may be mesophilic or thermophilic. For example, the recombinase may be derived from a myoviridae phage. The myoviridae phage may be, for example, T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2. In a preferred embodiment, the T4 recombinase UvsX may be used. The Rad systems of eukaryotes or the recA-Reco system of *E. Coli* or other prokaryotic systems may also be used.

Usually a recombinase will polymerise onto a single-stranded oligonucleotide in the 5'-3' direction. The invention as described herein relates to such a recombinase. However, the recombinase may polymerise in a 3'-5' direction and such recombinases may also be used in the method of the invention. In this case and with reference to the directionality of the components described, the reverse applies.

Recombinase accessory proteins may be included in the system, such as single-stranded binding protein (e.g. gp32) and recombinase loading agent (e.g. UvsY). In a preferred embodiment, the recombinase system comprises the T4 gp32, UvsX and UvsY. When such a system is used, all single stranded elements (i.e. primers and IO) become coated with the single stranded binding protein (e.g. gp32). The recombinase loading agent (e.g. UvsY) acts as a cofactor for the recombinase and coats the IO. The recombinase (e.g. UvsX) competently coats only the IO since only this element comprises a sufficient length to induce the process.

The recombinase (e.g. UvsX), and where used the recombinase loading agent (e.g. UvsY) and single strand DNA binding protein (e.g. gp32), can each be native, hybrid or mutant proteins from the same or different myoviridae phage sources. A native protein may be a wild type or natural variant of a protein. A mutant protein (also called a genetically engineered protein) is a native protein with natural or manmade mutations such as insertions, deletions, substitutions, or a combination thereof, that are at the N terminus, C terminus, or interior (between the N terminus and the C terminus). A hybrid protein (also called a chimeric protein) comprises sequences from at least two different organisms. For example, a hybrid UvsX protein may contain an amino acid from one species (e.g., T4) but a DNA binding loop from another species (e.g., T6). The hybrid protein may contain improved characteristics compared to a native protein. The improved characteristics may be increased or more rapid amplification rate or a decreased or more controllable amplification rate.

Other factors used to enhance the efficiency of the recombinase system may include compounds used to control DNA interactions, for example proline, DMSO or crowding agents which are known to enhance loading of recombinases onto DNA (Lavery P et. Al JBC 1992, 26713, 9307-9314; WO2008/035205). Whereas crowding agents such as PVA, gelatine or albumin are known to influence enzyme kinetics by increasing the effective concentration of reagents due to volume occupation (Reddy M K et. Al. Methods Enzymol. 1995; 262:466-76; Harrison B, Zimmerman S B. Anal Biochem. 1986 Nov. 1; 158(2):307-15; Reddy M K, Weitzel S E, von Hippel P H. Proc Natl Acad Sci USA. 1993 Apr. 15; 90(8):3211-5; Stommel J R et. Al. Biotechniques. 1997 June; 22(6):1064-6), DMSO, betaine, proline and detergents may enhance the systems by altering the Tm or secondary structure of the oligonucleotides in the assay.

Polymerase

The polymerases used in the process of the invention are preferably those with strand displacement activity. This activity is a well-known property of certain DNA polymerases (Sambrook et al., 1989, Molecular Cloning: A Laboratory Manual, 2nd edition, pp. 5.33-5.35, Cold Spring Harbor Laboratory, Cold Spring Harbor). The properties of the DNA polymerases, particularly the strand displacement activity of some of them, are given in detail by Kornberg and Baker, DNA Replication, 2nd edition, pp. 113-225, Freeman, N.Y. (1992). Strand displacement is not a property common to all DNA polymerases since some of them, like T4 DNA polymerases, are not capable of accomplishing strand displacement alone. Strand displacement may in these cases be imparted by the addition of the polymerases accessory proteins. Strand displacement activity was shown initially for the Klenow fragment of *Escherichia coli* DNA polymerase I (Masamune and Richardson, 1971, J. Biol. Chem. 246: 2692-2701), which confers on this enzyme the capability of initiating replication of nucleic acid from the 3'OH end of a cleavage site in a double-stranded DNA. This strand displacement activity has also been shown in thermostable DNA polymerases such as Tli DNA polymerase (Kong et al., 1993. J. Biol. Chem. 268: 1965-1975). In this case it has also been shown that mutated forms of this enzyme do not have exonuclease 5'-3' activity that has a higher strand displacement capacity. This strand displacement activity has also been shown for T7 DNA polymerase (Lechner et al., 1983. J. Biol. Chem. 258: 11174-11184) and for HIV reverse transcriptase (Huber et al., 1989, J. Biol. Chem. 264: 4669-4678).

Preferably, a DNA polymerase with no 5'-3' exonuclease activity is used to accomplish the amplification cycle according to the invention since the effectiveness of the strand displacement activity is greater in enzymes with no such exonuclease activity. The Klenow fragment of *Escherichia coli* DNA polymerase I is an example of a polymerase with no 5'-3' exonuclease activity, as are polymerases such as T7 DNA polymerase or Sequenase (US Biochemical). T5 DNA polymerase or Phi29 DNA polymerase can also be used. However, a DNA polymerase having this 5'-3' exonuclease activity can be used when it does not prevent the amplification process from being carried out. In this case, the yield of the amplification reaction can be improved by specific inhibition of the 5'-3' exonuclease activity of DNA polymerases under the reaction conditions employed.

Stand displacement may also be enhanced by the application of enzyme systems or other elements that stabilise single stranded rather than duplex DNA. Examples of such systems are the application of DNA helicases, stabilisation by single stranded binding proteins as well as the influence of the particular polymerase used in the system. It is essential that the method of enhancement of strand displacement does not interfere with the strand invasion system.

Suitable polymerases include polI or polI fragments or variants such as those from *E. Coli, Bacilus bubtilis, stearothermophilus* or T7 polymerases. Equally a polymerase holoenzyme complex can be used such as that described for phage T4. Preferred polymerases are klenow, exo-, a T7 polymerase or BST phi29 or pol-I of *bacillus subtilis* or a holoenzyme. In some embodiments and especially where a downstream element or a reverse complement are used it may be preferable that the polymerase does not have strong strand displacing activity as is the case for the klenow fragment of *E. Coli* polI. In other embodiments strong strand displacement activity of the polymerase may be an advantage.

ATP Regeneration System

Where a recombinase is utilised for the strand invasion step the system may have a requirement for a source of energy. The majority of these enzymes utilize ATP as the energy source but since ATP collates magnesium ions necessary for enzyme activity it is prudent to supply an additional ATP regeneration system rather than raise the concentration of ATP. ATP generation systems may involve various enzymes in the glycolytic or other biochemical pathways and together with ATP consumption these enzymes together with the SIS enzymes induce orthophosphate and or pyrophosphate accumulation concomitant with the production of AMP and ADP. The accumulation of inorganic phosphates is also able to chelate magnesium and may be deleterious to the system in numerous ways. The conversion of pyrophosphate to orthophosphate may be achieved by pyrophosphatases and orthophosphate conversion to less harmful organophosphates has also been variously reported.

Preferably the inorganic phosphate or orthophosphate conversion to organophosphate utilises sucrose and sucrose phosphorylase or other sugar phosphorylases. Alternatively nicotinamide riboside and purine phosphorylase may be used.

Since some ATP regeneration systems utilise ADP exclusively as a substrate, it may be an advantage to convert AMP produced by some recombinases to ADP using a myokinase. This also avoids premature depletion of the ATP resource. Under standard operating conditions described in the examples, the T4 recombinase does not produce AMP and this step can be omitted.

The ATP regeneration systems themselves generally use phosphocreatine with creatine kinase or phospho-phenyl-pyruvate and pyruvate kinase. Since the UVSX recombinase may burn up to 300 molecules of ATP in one minute and since 3 µM UVSX may be used, it is advantageous to use a system with 40-100 mM phosphocreatine.

In practice it may be advantageous to include one or more of the above energy sources in the reaction solution, for example, one or more of ATP, Phosphocreatine, Creatine Kinase, Myokinase, Pyrophosphatase, Sucrose, Sucrose phosphorylase.

General Considerations for Optimisation of the System

In practice when carrying out the method of the invention standard titration of the various components of the system shown in the standard operating procedure may be required to ensure optimal amplification. Titration of components includes proteinaceous metal ion and salt titrations. In the case of salts the nature of the cation and anion as well as the optimal concentration may be assessed to achieve optimal amplification.

Thus, various components may be included such as: magnesium ions; phosphocreatine and its counterion, pH adjusters, DTT or other reducing agents, BSA/PEG of various molecular weight distributions or other crowding agents, ATP and its counter ion, dNTP, Sucrose, Creatine Kinase, Myokinase, Pyrophosphatase, Sucrose Phosphorylase, UvsX, UvsY, gp32 (NEB, 10 mg/ml), Klenow, exo- or other polymerases.

The buffer system utilised in the amplification protocol should be compatible with all elements supplied to the system. Clearly optimum conditions for all components may not be achieved within a single buffered system. Numerous opportunities exist that may be used to balance the experimental condition such that the system works efficiently.

Primer and oligonucleotide design also impacts on the balance of the system since alteration in the length and melting temperature of the various primers and oligonucleotides, as well as the chosen amplicon length, can alter the balance of duplex separation and primer extension.

Melting temperature (Tm) is temperature that half of the population of identical duplex is separated. The length and sequence of a duplex relates to the Tm such that a longer duplex tends to have a higher Tm. Equally the buffer solution utilised during amplification may alter Tm since various salts and other components may alter the affinity between templates and primers (Chadalavada S. V. FEBS Letters 410 (1997) 201-205). In the context of this invention the Tm relates to the areas of a duplex that have not been invaded by an 10. Although the detail herein relates to systems developed to work at approximately 40° C., it is possible to develop systems that function at differing temperatures, for example from about 21 to 50° C., preferably from about 25 to 45° C., most preferably from about 37-40° C. Consequently the lengths and sequences of the target and primers may be adjusted accordingly. Where the template under investigation is negatively supercoiled then these tendencies do not apply to the initial template since negatively supercoiled DNA can be treated as if it is single stranded DNA. In the first round of amplification it may be necessary to heat or otherwise chemically/enzymatically denature or cleave the target to initiate the amplification process. An additional primer called a bumper primer maybe used to initiate the first round of amplification as previously reported (Nuovo G. J; Diagn Mol Pathol. 2000 (4):195-202). Furthermore if the system enables the upstream or the downstream primer to extend slowly in the first rounds of amplification then no additional features are necessary but there will be a lag phase caused by the resistance to the initial amplification event.

Amplification Method

The following part of the description will describe one embodiment of the invention wherein the method relies on a strand invasion system (SIS) induced by a recombinase. A recombinase reacts with a single stranded oligonucleotide substrate and enables it to invade a complementary strand within a duplex nucleic acid, displacing the other outgoing strand (OS) of the duplex.

The essential principal of the invention is that an oligonucleotide (IO) is presented that invades a duplex nucleic acid target. The consequence of this event is that the strands of the target duplex are separated and dissociate in the template region cognate to the invading oligonucleotide but also in an area outside but proximal to the invasion site and this allows terminal primers to bind to the component strands, and extend, which result in two duplex copies. The process repeats itself recursively with resultant exponential amplification of the target.

In one embodiment of the invention a duplex target nucleic acid is invaded in its mid region by a single stranded non-extendible oligonucleotide (IO) by the action of a recombinase. Invasion by the oligonucleotide disturbs the duplex stability to the extent that the duplex falls apart and becomes single stranded. This exposes binding sites for upstream and downstream primers (that are not recombinase substrates) and these extend onto the separated strands creating two copies of the duplex (FIG. 2).

Figure 2:
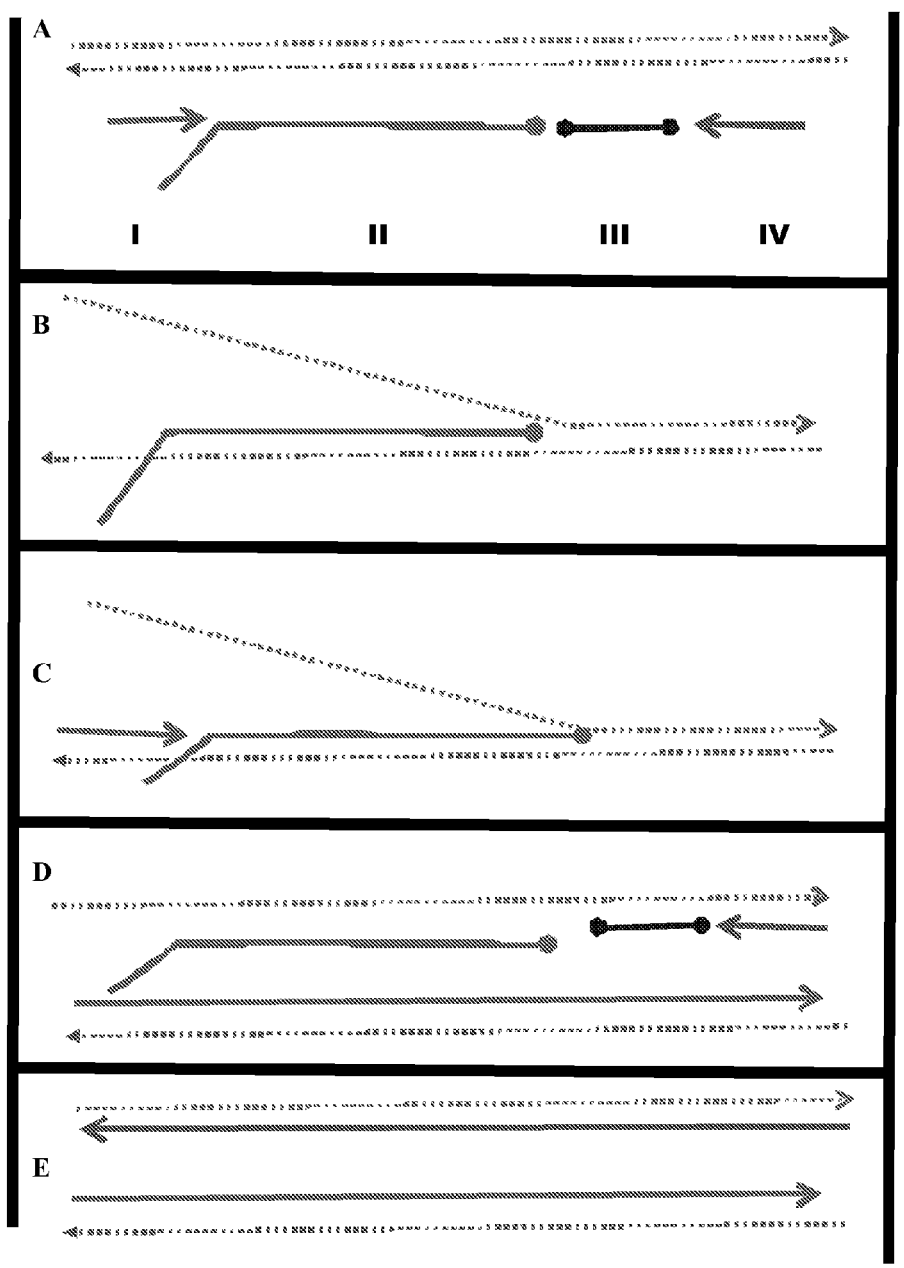
FIG. 2 demonstrates the basic amplification system of this invention together with an optional probe based detection system.
Figure 3:
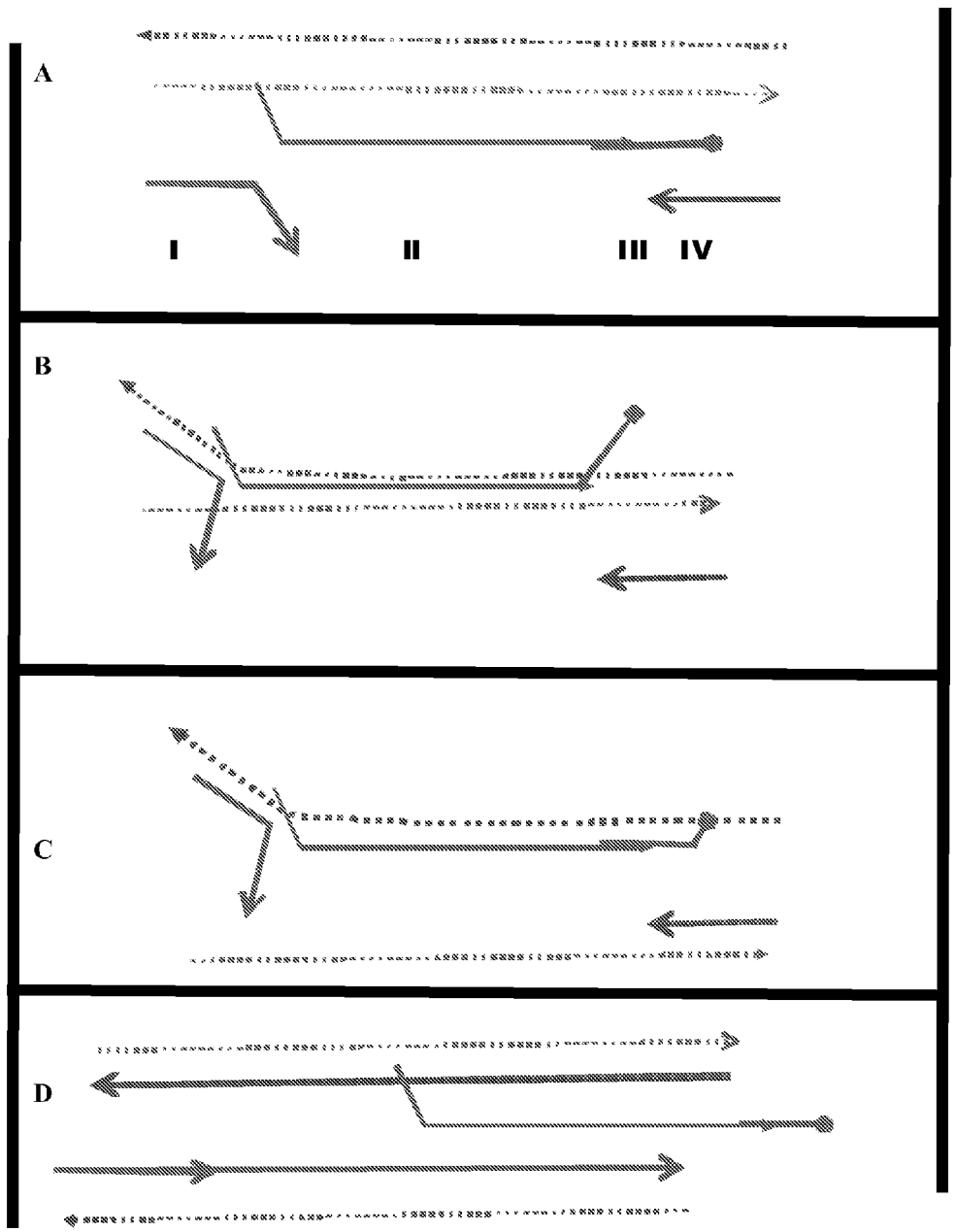
FIG. 3 shows an amplification method where a downstream element is used to protect from non-specific amplification products.
Figure 4:
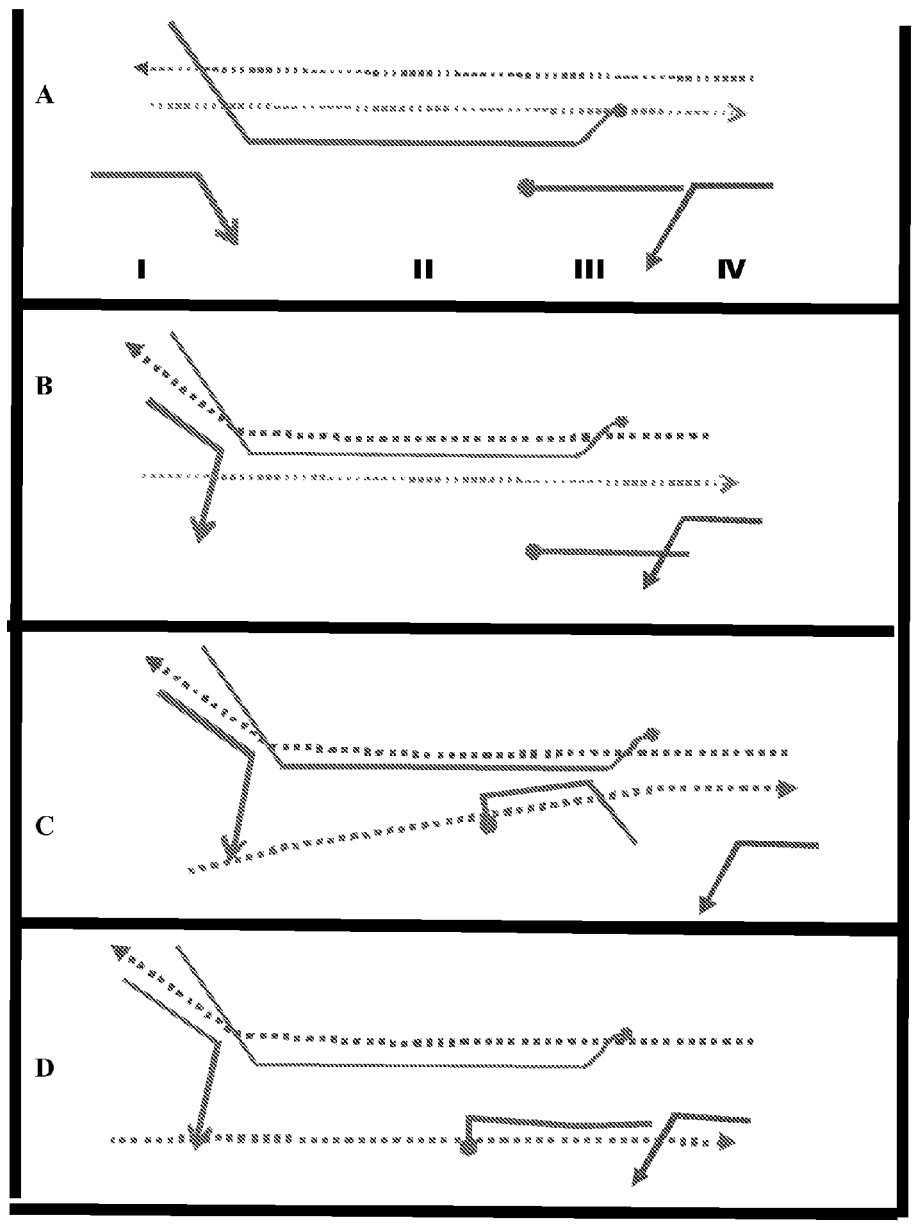
FIG. 4 shows an amplification method utilizing a reverse complement oligonucleotide such that non specific products cannot be formed.
Figure 5:
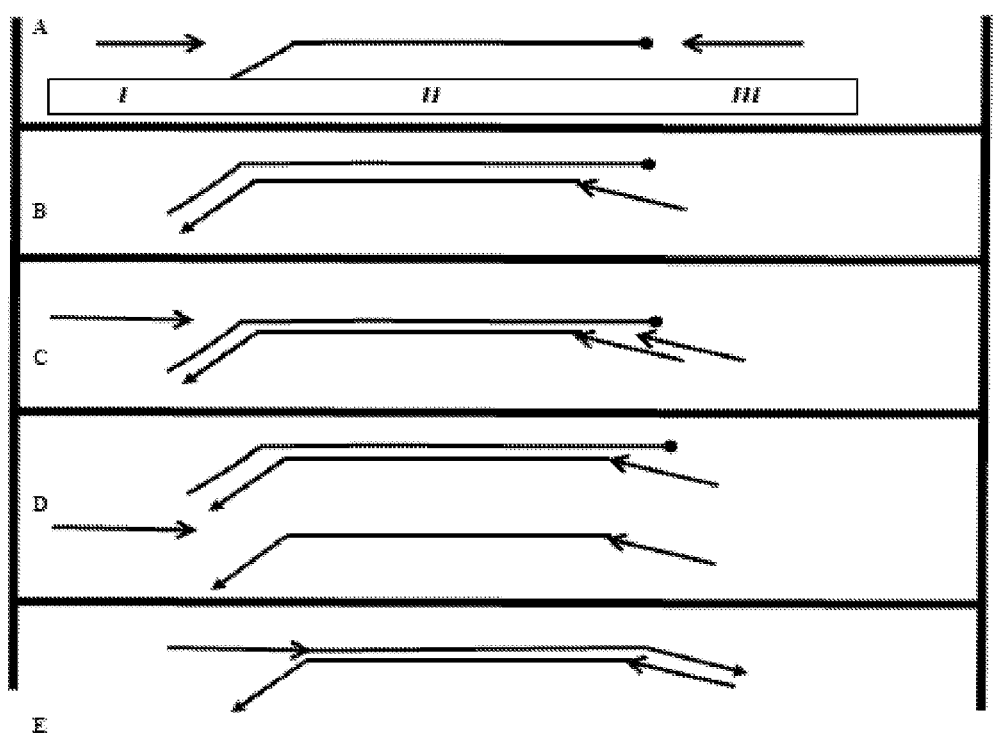
FIG. 5 shows the sequence of events that can lead to primer artefacts in a tripartite system.

FIG. 2 demonstrates the basic amplification system of the invention together with an optional probe-based detection system. This system is protected from non-specific amplification to some extent but non-specific products may be formed after prolonged incubation as shown in FIG. 5 (discussed below). FIGS. 2 to 4 are described in connection with the T4 gp32, UvsX and UvsY recombinase system but any recombinase system, or other strand invasion system may be used.

2A: The elements of this system are shown as I-IV. A duplex template is shown as dotted lines. I represents an upstream primer that is not a substrate or is only a minimal substrate for the SIS as described (i.e. it does not bind recombinase). II shows the central component of the system, the IO, which can be extendable by the action of a polymerase or non-extendable. This nucleic acid element is a substrate for the SIS in that it binds recombinase and invades the target duplex. It does not need to be acted on by a polymerase. This element may also optionally comprise an extended 3' or 5' tail that is not cognate to the sequence that is invaded. The 5' region of the cognate area of the invading oligonucleotide is close enough to the duplex terminus such that the melting temperature of the residual duplex is below the ambient temperature of the system and results in dissociation of the residual upstream duplex after binding. III shows the potential site for an optional probe system such as a T7 exonuclease sensitive probe or a molecular beacon. IV represents the downstream primer that is not a substrate or only a minimal substrate for the SIS.

All single stranded elements of the system become coated with the single stranded binding protein GP32. UVSY which is a cofactor for UVSX also coats the IO. The GP32 coated elements have a reduced capacity for branch migration. UVSX competently coats only the IO since only this element comprises a sufficient length to induce the process.

2B After coating the IO (II) with recombinase, it is able to invade the duplex. The duplex separates and becomes single-stranded in the region of invasion and also in adjacent regions, usually around 15 to 20 nucleotides in length. This releases the upstream terminal end of the duplex nucleic acid 2C: The upstream primer (I) is able to bind to the released strand. Primer concentration temperature and other system components such as denaturants are optimised such that the primer binds efficiently despite its proximity to its melt temperature.

2D: The upstream primer (I) extends which stabilizes its product and displaces the IO (II). This recreates the original duplex. The downstream primer (IV) together with the optional probe (III) is able to bind to the displaced downstream region. The system can be optimised such that the upstream or downstream primer concentrations are asymmetric and by this mechanism an excess of the downstream primer ensures that a single stranded excess of downstream product is induced at the end of the reaction and that the binding site for the probe is available 2E: The downstream primer extends doubling the duplex number.

Usually two complementary oligonucleotides bind together with an affinity that depends on the length and sequence of the cognate region. The two strands tend to fall apart only above a particular temperature and this is called the melt temperature (Tm). The length of the cognate region is proportional to the Tm. The Tm is also affected by the magnesium and monovalent salt concentration and is also reduced in the presence of single stranded binding proteins. The transitory presence of a recombinase on an oligonucleotide will increase its Tm. The relevant melt temperature parameters are therefore generally assessed empirically.

A duplex may be invaded by a recombinase-coated oligonucleotide and this is dependent on it being cognate to one strand of the invaded duplex. The other strand of the duplex is nominated as the outgoing strand (OS) and is essentially separated from the cognate strand of the duplex and becomes single-stranded. Consequently where the residual duplex outside the invaded region has a length and sequence such that the Tm is below the ambient temperature then the complete duplex will dissociate producing two single stranded termini which can bind terminal primers.

Most recombinases polymerise onto an oligonucleotide from its 5' region towards its 3' region and once the coated oligonucleotide invades a duplex then the SIS continues to polymerise onto the duplex 3' to the invading oligonucleotide (downstream). The coated elements of an invaded system are held together more tightly than an uncoated region. It is also notable that a primer bound to a template that is coated with a recombinase cannot be extended until the recombinase has depolymerised and has been removed.

As a consequence of the above observations, if the template duplex terminus upstream of the IO is close to the invaded region, then the terminus will separate since it is not coated with the recombinase and a primer may bind and extend displacing the IO such that it can be re-used by the system. Under the same circumstances, the downstream terminus will be held together until the recombinase depolymerises/falls off which is also in a 5' to 3' direction. If the Tm of the downstream terminus is higher than the ambient temperature then its strands will remain associated even after depolymerisation of the recombinase but the strands will still be separated as the upstream primer extends and displaces the strands of the original duplex. This will enable a downstream primer to subsequently bind and extend (FIG. 2).

If the upstream terminus is not close to the invaded region but the proximity of the downstream terminus is close enough to allow melting then it might be expected that the downstream terminus would separate after depolymerisation of the recombinase. Surprisingly this is not the case since the closed upstream terminus of the duplex branch migrates as the recombinase depolymerises displacing the invading oligonucleotide, repositioning the outgoing strand onto its partner and reforming the original duplex and does not give an opportunity for the downstream primer to bind. Branch migration is rapid in this scenario since the outgoing strand remains wrapped around the complex in a plectonemic conformation and remains highly associated with its cognate strand even when displaced.

The consequence of these events is that for a system to be viable such that the SIS enables a duplex to be separated then the upstream terminus of a target duplex must be separated during the strand invasion event. This is achieved by ensuring that the upstream region of the duplex proximal to the invasion site has a melting temperature close to or below the ambient temperature. This is easily determined by the skilled person using standard techniques but will be influenced by system components such as single stranded binding proteins, metal ion concentrations and salt concentration.

Accordingly, the IO should preferably be designed such that it is complementary to the target molecule leaving only about 10-20 bases, preferably about 15-17 bases, on either side of the cognate region. Thus, for example, where the application is performed at 40° C. a non extendible IO is supplied to the system such that it leaves 10-17 bases of duplex on either side of the cognate region. On invasion by the IO the upstream terminus (in relation to the invading oligonucleotide) of the duplex melts whereas the 3' terminus is held together due to the invasion dependent polymerisation of the recombinase onto the downstream duplex. The upstream primer binds to the melted upstream terminus of the duplex and is extended, thereby displacing the IO. The downstream end of the duplex can either be separated by the continued extension of the upstream primer or it may be short enough so that when the recombinase depolymerises it also melts.

The scenario above depicts the consequence of a recombinase that polymerises in the 5'-3' direction (upstream to downstream). The description herein describes amplification with this type of recombinase. Where a recombinase is utilised that polymerises in the opposite direction then the configuration of the system is reversed. Most recombinases prefer a region of 12-15 bases at the upstream terminus of an IO to facilitate seeding of the recombinase and this feature may be incorporated such that an IO comprises an upstream non-cognate region.

In the above-described methods, although amplification artefacts are minimized, it is plausible that a primer could non-specifically copy onto the IO and that the product of this extension could be displaced, copying onto a further primer as shown in FIG. 5.

FIG. 5 shows the mechanism by which primer artefacts can occur in a tripartite system that does not include a downstream element 5A: The system components that induce artefactual amplification comprise the upstream primer (I), the intermediate oligonucleotide (II) and the downstream primer (III 5B: A downstream primer may occasionally copy onto the intermediate oligo 5C: Any additional oligonucleotide primer may copy onto the intermediate upstream of the position that the downstream primer occupied.

5D: Extension of the additional oligonucleotide primer will result in the displacement of the product of the downstream primer extension 5E: Finally, if an upstream primer copies onto the displaced product then an amplifiable unit may be produced.

These events are more complex than those involved in the production of primer dimer artefacts for the two primer system described in FIG. 1 and as a result the sensitivity of the system for assessing the presence of test template is improved over systems dependent on only two primers.

Although such an event is rare the consequent oligonucleotide sequence would potentially be an amplifiable unit. However, this eventuality is abrogated by embodiments of the invention discussed below. In order to overcome any potential for non-specific amplification the following phenomenon may be utilised.

Where only one end of the duplex is separated due to the invasion by the IO then a cognate primer can bind to the dissociated terminus but the partially tethered outgoing strand remains in close proximity. Since the outgoing strand also comprises an identical region to that of the primer it is able to compete with the incoming primer for binding to the template. Additionally the tethered terminus may also branch migrate after depolymerisation of the recombinase, reinstating the original duplex before a primer bound to the separated terminus has an opportunity to extend. Under these circumstances and where only the upstream terminus is melted then extension of the upstream primer may be compromised and become dependent on the separation of the downstream termini such that the strands of the duplex are no longer tethered and fall away. By this process, competition by the outgoing strand is abolished. A system can therefore be designed such that despite the separation of the upstream aspect of the duplex, the upstream primer is only competent if the downstream termini have also been separated. The dependence of the system on the separation of both termini adds specificity to the system and can be achieved by altering the competency of the upstream primer in favour of reinstatement of the outgoing strand or by using a polymerase at low concentrations or with weak strand displacement activity (Klenow exo-activity) as this will also effect the balance of primer extension with duplex reinstatement. Under any circumstances it is found that amplification is substantially faster where the two strands of the duplex are separated. Therefore artefactual amplification, that does not impart this quality, will be outpaced if the amplification of the specific target induces strand separation.

The competence of the upstream primer can be altered by several mechanisms, for example:

(i) The upstream primer may be designed to overlap with the invading IO. The region of overlap is preferably about 5 to 10 nucleotides. Extension of an overlapping primer will rely on the preliminary branch migration of the primer onto the template displacing the IO. Under some circumstances, and specifically where single stranded binding proteins are present, branch migration is slow and pauses the extension of the primer such that competition between the binding and extension of primer versus the re-instatement of the original duplex may be in favour of reinstatement. Another advantage of this embodiment is that the termini proximal to the IO do not separate if the length is above 18-23 bases. As such the melting temperature is above the ambient temperature of the reaction where this is about 40° C. The primer described in this construct has a Tm that is above this figure but creates a terminus with a Tm below the ambient temperature. If such a primer is used then it can bind to the cognate terminus of the melted duplex and its 3' region will branch migrate to onto the invaded aspect of the duplex if it is cognate and subsequently extend by the action of a polymerase. If the primer becomes part of a non-specific/template independent product then unless it is positioned perfectly with the IO region, it may not be a viable amplification unit.

(ii) The upstream primer may be temporarily blocked and rely on an enzymatic cleavage prior to extension. This is exemplified by a 3' blocked primer comprising an RNA base proximal to the 3' terminus together with RNAse H. Analogous systems using alternative endonucleases may be used as can any mechanism that slows the progress of the primer.

In the embodiment described above the amplification becomes dependent on the melting of the downstream terminus as well as the upstream terminus. Systems designed to rely on melting of the downstream terminus can add absolute specificity to the amplification. If the Tm of a downstream primer is higher than the ambient temperature then the downstream terminus will not melt and furthermore non-specific artefactual product will not amplify. It is an advantage to use such primers but the problem remains as to how a primer with a Tm above the ambient temperature of the reaction can induce a terminus that will separate. This is accomplished by utilizing other additional sequence dependent elements to melt the downstream terminus.

For example, the downstream tethered termini may be separated by the binding of one or more additional oligonucleotides which facilitate the separation of the target duplex by the intervening oligonucleotide and whose function depends on the IO invasion step. The value of this approach is that such an oligonucleotide is designed to bind and separate the duplex but is neither a polymerase nor a recombinase substrate. Such an oligonucleotide cannot participate in the production of a primer artefact since it is not a polymerase substrate which is important as shown in FIG. 5. Preferably the additional oligonucleotide binds to the strand released by the IO and branch migrates into the proximal duplex nucleic acid. Importantly where its function demands branch migration and where branch migration is found to be inhibited by single stranded binding proteins then it can be designed such that it does not bind significantly to single stranded binding proteins. This approach is exemplified by:

(i) The IO may comprise sequence which is an extension of its 3' terminus (downstream element, DE) which is cognate to the target terminal region, as shown in FIG. 3 and discussed below.

In this embodiment, the DE comprises elements that are not a polymerase substrate and optionally neither recombinase nor SSB substrates. Typically this may be imparted by the use of 2' modified nucleotides. Typical modifications of the 2' position include hydroxylation, methylation and alkylation. It may alternatively be induced by modification of the base sugar or phosphate component that results in template and/or primer incompetent qualities. Suitable elements include RNA and RNA analogues, such as locked nucleic acid (LNA), morpholino, peptide nucleic acid (PNA) and other nucleic acid modifications that enable hybridization. These oligonucleotides differ as they have a different backbone sugar but still bind according to Watson and Crick pairing with RNA or DNA, but cannot be amplified as polymerase is unable to recognise them. It is important that the element is able to hybridise to its target sequence.

The DE may be an extension of the IO and is able to branch migrate downstream of the invading section disturbing the remaining duplex and leaving an intact area of duplex with a Tm below the ambient temperature, separating the duplex such that a primer can bind and extend. There is a cognate overlap between the downstream primer and the DE. It is important that the DE and downstream primer cannot copy onto each other and as such the DE should be neither a primer, nor a template substrate for a polymerase, i.e. it should not allow a primer to bind and extend upon this region beyond its junction with the IO and onto the IO. The 3' terminus of the DE may optionally have additional spurious bases and/or be blocked from extension to facilitate this, for example by placing a non-extendible unit at it 3' terminus or by the addition of non-cognate bases in this region. Typically extension of the 3' terminus is blocked by incorporating one or more of several modified nucleotides. Typically these will incorporate a 3' modification of the terminal nucleotide. Examples of these modified nucleotides are dideoxynucleotide nucleotides, 3' amino-allyl, 3'-carbon spacers of various lengths, nucleotides incorporated in a reversed orientation (3'-3' linkage), 3' phosphate, 3'biotin, 3' salyl, 3'-thiol. Alternatively the terminus may comprise nucleotides incompatible with extension be a polymerase due to their poor substrate capability such as PNA or LNA or 2'-5'-linked DNA or 2'-O-methyl RNA.

(ii) An additional oligonucleotide (reverse complement, RC) maybe supplied that has a 3' region cognate to the 3' region of the IO and a 5' region cognate to the target termini as shown in FIG. 4 and discussed below.

The reverse complement has a 3' region cognate to the 3' region of the IO and binds to the outgoing template strand in this region. The 5' terminus of the RC is cognate to the target duplex proximal to the IO region and on the outgoing strand. The 3' region should be long enough to bind to the outgoing strand and stable enough to induce branch migration of its 5' aspect into the proximal duplex. Typically this 3' region would be 10-20, preferably 10-14, bases in length.

It is important that it does not interfere significantly with the function of the IO and since it is cognate to this oligonucleotide it may be preferable to include bases which are not recombinase substrates such as 2' modified elements, RNA or 2-O-methyl RNA or PNA or LNA. Furthermore it is helpful that this oligonucleotide is not a template for a polymerase. The 5' region should be able to branch migrate into the proximal duplex in the presence of the system constituents, in a similar fashion to the downstream element. To this end it is preferable that this area comprises modifications that are not a substrate for single stranded binding proteins.

The RC is pointing in the same direction as the downstream primer and as such its interactions with this element are not important. The RC binds to the opposite strand of the duplex compared with the downstream element and as such the downstream primer will overlap with but not be cognate to the RC. Since the RC is cognate to part of the IO it may be an advantage for the IO to be blocked from extension (e.g. with spurious 3' bases or as described above) and/or have some additional bases at its 3' terminus that are not cognate to the template. This will prevent the IO from forming an amplifiable unit. The same is true for the 3' terminus of the RC and to this end the RC may be blocked at its 3' terminus to further avoid extension and may comprise some additional bases at its 3' terminus that are not cognate to the template.

FIG. 3 shows an amplification method where a downstream element is used to protect from non-specific amplification products.

3A: The elements of this system are shown as I-IV. A duplex template is shown as dotted lines. I represents an upstream primer; II an intervening oligonucleotide (IO); III a downstream element (DE) which is a 3' extension of the IO and may comprise non-cognate bases at its very 3' terminus. In contrast to the IO, this downstream element is not a substrate for a polymerase and may not be a substrate for the recombinase. IV represents a downstream primer.

The basis of the amplification is similar to that shown in FIG. 2 but in this system both of the terminal primers have a melting temperature that is above the ambient temperature of the system and consequently will not amplify unless the constraints of this system are met.

The upstream primer overlaps the IO and the downstream primer overlaps the DE and is therefore partially cognate to this element.

All single stranded elements of the system become coated with the single stranded binding protein GP32 although this is not necessarily the case for the DE. UVSY which is a cofactor for UVSX also coats the IO. The GP32 coated elements have a reduced capacity for branch migration.

UVSX competently coats only the IO since only this element comprises a sufficient length to induce the process.

3B: The recombinase-coated IO invades the duplex melting the upstream terminus. The downstream terminus is not melted since its Tm is above the ambient temperature and also because UVSX polymerizes onto this area clamping the duplex together. The upstream primer binds but does not extend immediately because its 3' region overlaps the IO and must first branch migrate. It is in competition with the tethered outgoing template strand which outcompetes the primer for binding and the system remains incompetent. It is also possible that the tethered downstream terminus may branch migrate backwards closing the original duplex after the recombinase has depolymerised but either way, the system will not adequately amplify.

3C: The DE branch migrates into the downstream duplex and since the Tm of the remaining downstream duplex is below the ambient temperature it is separated. The UVSX depolymerizes and since the upstream terminus is bound to primer the duplex is completely separated.

3D: This enables the downstream primer to bind and extend and also gives the upstream primer the opportunity to branch migrate and extend creating two copies of the duplex.

Notably, any primer artefact would need to comprise a binding sequence for the DE. Since the DE is composed of elements that are not substrates for a polymerase, this does not occur.

FIG. 4 shows an amplification method utilizing a reverse complement oligonucleotide such that non-specific products cannot be formed.

4A: The elements of this system are shown as I-IV. A duplex template is shown as dotted lines. I represents an upstream primer; II an intervening oligonucleotide with non-cognate bases at its 3' terminus; III reverse complement with non-cognate bases at its 3' terminus and IV a downstream primer.

In this system both of the terminal primers have a length that is above the critical melting temperature of the system and consequently will not form non-specific artefacts unless the non-specific artefact is identical to the target template.

The upstream primer overlaps the IO in the same direction. The downstream primer does not overlap the IO but does overlap an additional element, the RC. The RC is neither a polymerase nor a recombinase substrate and overlaps both the downstream primer and the IO. As such the downstream primer comprises the 3' terminus with a sequence identical to a region of the 5' area of the RC. The RC comprises a 5' sequence similar to that of the downstream primer and a 3' sequence complementary to the IO.

All single stranded elements of the system except for the DE become coated with GP32. UVSY which is a cofactor for UVSX also coats these elements. The coated elements have a reduced capacity for branch migration. UVSX competently coats only the IO since only this element comprises a sufficient length to induce the process.

4B: The recombinase coated IO invades the duplex melting the upstream terminus since it is below the critical temperature. The downstream terminus is not melted since it is above the critical temperature and also because UVSX polymerizes onto this area clamping the duplex together. The upstream primer binds but does not extend immediately because its 3' region overlaps the IO and must first branch migrate. It is in competition with the tethered outgoing template strand which outcompetes the primer for binding and the system remains incompetent.

4C: The UVSX de-polymerizes but the duplex strand remains partially melted. This enables the RC to bind to the IO and then branch migrate into the downstream duplex.

4D: Since the remaining duplex is below the critical temperature it is separated and falls away. This enables the downstream primer to bind and extend and also gives both the downstream and upstream primer the opportunity to branch migrate and extend creating two copies of the duplex.

Probes

Any of the methods described above may further comprise monitoring the amplification by measuring a detectable signal. The detection system may be attached to one or more oligonucleotides that are part of the amplification system. The detection system may be fluorogenic. A sequence may be generated during amplification which is cognate to the signal generating system.

Numerous probe based detection systems are known in the art and described elsewhere, e.g. WO 2006/087574. These systems usually consist of dual labelled fluorescent oligonucleotide comprising a FRET pair of a fluorophore and an acceptor moiety that maybe a fluorophore or a fluorescent quencher. The probe binding sequence may be part of the amplicon downstream of the IO as shown in FIG. 2 or it may be part of the primers, IO, the RC and/or the DE. All of these elements may comprise non-cognate bases and these may be designed such that they are captured by exogenous elements to localise amplified units. This is common to lateral flow systems.

Intercalating dyes such as Sybr green I and thiazole orange are able to signal the general process of DNA amplification. Alternatively or additionally a probe may be used that signals amplification of a particular amplicon. As such probe based systems may be used to multiplex several amplification processes in a single tube. This is achieved by utilising probes for each system with different types of output. This is exemplified by different wavelengths of fluorescent emission for each probe. Multiplexing is also an important part of the process of including internal negative and positive experimental controls.

Example of probe systems include the following:

(a) A fluorophore may be attached to the primer and this may be used as a Fret acceptor where the system includes a general intercalating dye.

(b) The fluorophore may be attached to the primer such that there is a detectable change in fluorescence when the primer is incorporated into the amplification product. This can be achieved by placing two or more fluorophores in close proximity so that they are self quenched or ground state quenched until incorporated into an amplification product.

(c) A fluorophore and a quencher or acceptor fluorophore may be incorporated into the IO or its DE such that there is a detectable change in fluorescence when IO is incorporated into an amplification product.

(d) A fluorophore acceptor/quencher (FRET) pair may be inserted into an element of the amplification system such that they are separated by a cleavable element and where the moieties of the FRET pair are separated by the cleavable element and where the cleavable element is acted on by a duplex specific nuclease. If the element is incorporated into an amplification product then the cleavage of this element will induce complete separation of the FRET pair consequently enhancing fluorescence of the system. The cleavable element maybe part of the IO or it may be part of the primer system or an additional element added to and cognate to the amplicon of the system.

Where the cleavable element is part of the primer system then the cleavable element may be at the 5' end of the primer binding site or at the 3' end of the primer binding site. If the cleavable element is placed at the 3' end of the moieties binding region then it may be advantageous to place non cognate bases three prime to the cleavable element and these bases may comprise the attachment of either the fluorophore or a quencher/acceptor. A primer with these qualities may be designed such that is not a part of the template amplification system but will be included in any artefactual amplification. A primer with these qualities can be used as a negative control for instance where it has an area cognate to the IO at or near its 3' terminus resulting in the artefacts described in FIG. 5.

The cleavage enzyme is exemplified by an RNASE-H or 8-oxoguanine or an abasic endonuclease. Typically the cleavable element will comprise RNA, 8-oxoguanine or an abasic site. The RNASE-HII family of enzymes including that of *T. kodakaraensis* recognise a single RNA substrate in a DNA-RNA duplex and enables a single RNA base to be inserted into its cognate element. Additionally, the cleavage enzyme maybe a 5'-3' exonuclease such as T7 gene6 and in this case the system is protected from the action of this enzyme by the application of phosphorothioate elements excepting the 5' aspect of the oligonucleotide that contains the fluorophore which is cleaved.

Where the cleavable element is inserted into the primer then it may be to the 5'side of the primer template binding site or 3' to this site. Where the cleavable base is at the 3' end of the primer binding site then it may be placed on the last cognate base or either side of this base. All bases 3' to this element may be non-cognate to the template and the 3' terminus may be blocked to extension until acted on by the RNASE-H or other endonucleases. Clearly, it is important that after cleavage either the fluorophore donor or acceptor are removed from proximity to its partner and this is achieved by ensuring that the melting temperature at one side of the cleavage unit is below the ambient temperature of the system.

(e) The fluorophore and quencher or acceptor fluorophore may be incorporated into different elements such that there is a detectable change in fluorescence when incorporated into an amplification unit.

In a further embodiment the invention provides a kit for isothermally amplifying a nucleic acid target molecule comprising an upstream primer, a downstream primer, a strand invasion system and an oligonucleotide, wherein the upstream and downstream primers are not substrates for the strand invasion system during the amplification process and do not amplify the target molecule independently of the strand invasion system, wherein the oligonucleotide is a substrate for the strand invasion system. Each element of this kit, included preferred features, is discussed in detail above. For example, preferred features may include that the strand invasion system comprises a recombinase system and/or that the oligonucleotide comprises a downstream element at its 3' terminus.

EXAMPLES

Protocol

Reagents and Solutions:
UVSX and UVSY were purified as previously described (Timothy Formosa and Bruce M. Alberts; JBC Vol. 261, 6107-6118, 1986).
RNASEHII-KOD-I was purified as previously described (Haruki M et. al. J Bacteriol. 1998 December; 180(23): 6207-14).

Assays were assembled from the following concentrates.
Magnesium buffer. 100 mM Tris; 100 mM Mg-Acetate; 20 mM DTT; pH 8.0
500 mM (di-Tris-)Phosphocreatine (Sigma) pH to 7.8 with ammonium hydroxide.
200 mM DTT in $H_2O$
100×BSA (10 mg/ml) in $H_2O$
100 mM ATP-disodium salt (Jena Biosciences) in $H_2O$
10 mM dNTPs (Sigma D7295)
50% PEG 1000 (w/v) (Fluka) in $H_2O$
2 M Sucrose (Fluka) in $H_2O$
Creatine Kinase, Type I from Rabbit muscle (Sigma C3755) Dissolved to 10 u/μl in 40% glycerol/50 mM KAc pH8
Myokinase, from Chicken muscle (Sigma M3003) Dissolved to 9 u/μl (200×) in 40% glycerol/$H_2O$
Pyrophosphatase (Sigma 11643) Dissolved to 0.4 u/μl (200×) in 40% glycerol/$H_2O$
Sucrose Phosphorylase (Sigma S0937) Dissolved to 0.4 u/μl in 40% glycerol/$H_2O$
UvsX, UvsY; 100 μM in 300 mM K-Acetate; 50% glycerol.
gp32 (NEB, 10 mg/ml)
Klenow, exo⁻ (Jena Biosciences, 50 u/μl) used at final concentration of 0.05 u/μl

| Component | Final reaction conc. |
| --- | --- |
| Tris pH 8 | 10 mM |
| Mg-Acetate | 10 mM |
| BSA** | 0.1 mg/ml |
| DTT** | 5 mM |
| DMSO** | 5% |
| PEG 1000** | 5% |
| Sucrose** | 150 mM |
| ATP | 2 mM |
| dNTPs | 200 μM |
| Sybr Green** | 1:100000 |
| Oligonucleotides | As show in examples |
| gp32 | 0.5 uM |
| Phosphocreatine (diTRIS) pH to 7.8 With KOH | 75 mM |
| Creatine Kinase | 1 uM |
| Myokinase** | 1 uM |
| Pyrophosphatase** | 1 uM |
| UvsY | 1.5 uM |
| UvsX | 1.5 uM |
| Sucrose phosphorylase** | 1 uM |
| Klenow | 0.1 uM |
| Template DNA | As shown in examples |

**components found to optimise but are not essential for amplification.

Test template was added to a mixture of the reaction components except for UVSX and klenow. The reaction components were incubated with test sample for 5 minutes at the working temperature (40° C.) and the UVSX and klenow were added. Total sample volumes were 20 ul placed into a low volume 384 well micro-titre plates. Fluorescence was assessed on a BMG-fluostar-II. Fluorescence was monitored at one minute intervals by exciting at 480 nm and reading emission at 520 nm for Sybr green fluorescence (unless otherwise stated).

Example 1

Two-Primer System, No Intermediate Oligonucleotide (Prior Art System)

Figure 6A:
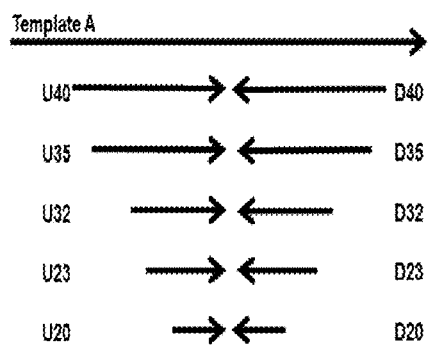
FIG. 6A shows template/primer configurations.

The protocol used is the same as that described above unless otherwise stated. The oligonucleotide constituents comprised two primers at a final concentration of 150 nM together with Template A. Template/primer configurations are shown in FIG. 6A. Template A concentrations were 1 nM unless stated and amplification was followed by Sybr green fluorescence.

Figure 6B:
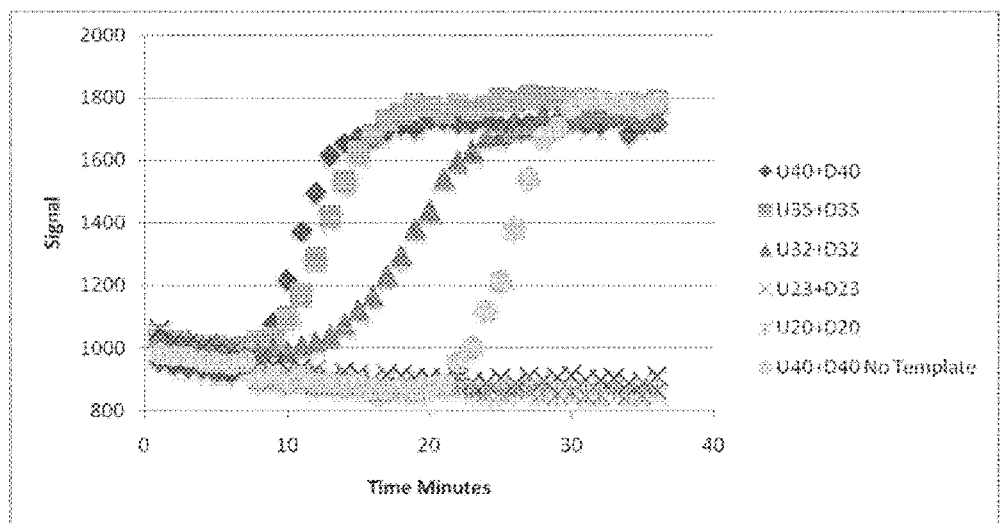
FIG. 6B shows amplification in a 2-primer system (measured by Sybr Green fluorescence).

The results are shown in FIG. 6B. In this two primer system, amplification occurred where the primer length was equal to or in excess of 32 bases (U32+D32; U35+D35 and U40+D40). No amplification occurred with the 23 and 20 base primers (U23+D23 and U20+D20). Primer dimer artefacts occurred as shown for the 40 base primers (no template). These artefacts generally emerged at the same time as template concentrations of 10 pM and this limited the sensitivity of the technique to this level.

Example 2

Three-Primer System (Using Two Primers and a Non-Extendible Intermediate Oligonucleotide)

Figure 7A:
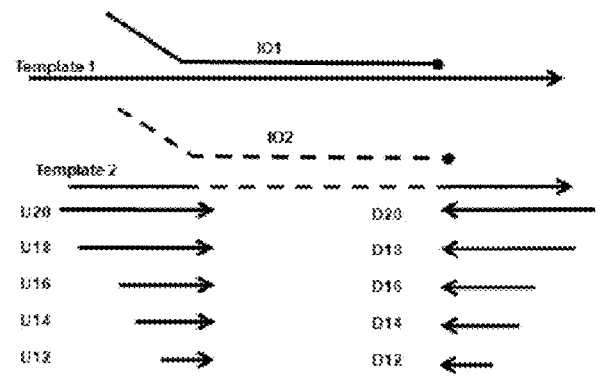
FIG. 7A shows template/primer/oligonucleotide configurations.

The protocol used is the same as that described above unless otherwise stated. Template/oligonucleotide/primer configurations are shown in FIG. 7A. Primers were U16 and D16 used at a concentration of 200 nM each. Intermediate oligonucleotide concentrations were 150 nM and template concentrations were 100 fM. The signal was produced by Sybr green fluorescence.

Figure 7B:
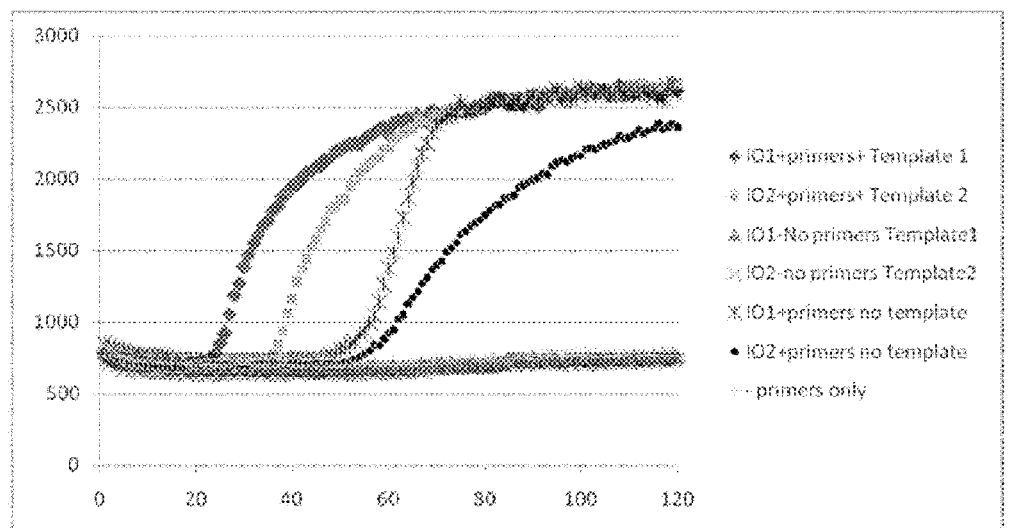
FIG. 7B shows amplification in a tripartite system (measured by Sybr Green fluorescence).

FIG. 7B demonstrates amplification of the three oligonucleotide system configured as shown in FIG. 7A using upstream and downstream primers U16 and D16 respectively. Amplification is achieved with primers of 16 bases in length and is dependent on the non-extendible oligonucleotide (IO). The system is less prone to artefacts. The primers of 16 BP are able to amplify if the intermediate oligo is cognate (IO1+primers+Template1; IO2+primers+Template2)). Primers will not amplify alone (primers only); neither will intermediate amplify alone (no primers). Artefacts can occur in the absence of template in some systems limiting the sensitivity to between 1 and 10 fM giving a sensitivity of one thousand times greater than a two primer system.

Example 3

Primers in a Tripartite System must be below 20 Bases in Length under the Coditions Used (Dependent on Melt Temperature of the Primer and Ambient Temperature and Denaturation Agents)

The protocol used is the same as that described above unless otherwise stated. Primers were of various lengths were used at a concentration of 200 nM each. Intermediate oligonucleotide (IO1) was used at 150 nM and template concentration was 100 fM. The signal was produced by Sybr green fluorescence.

Figure 8:
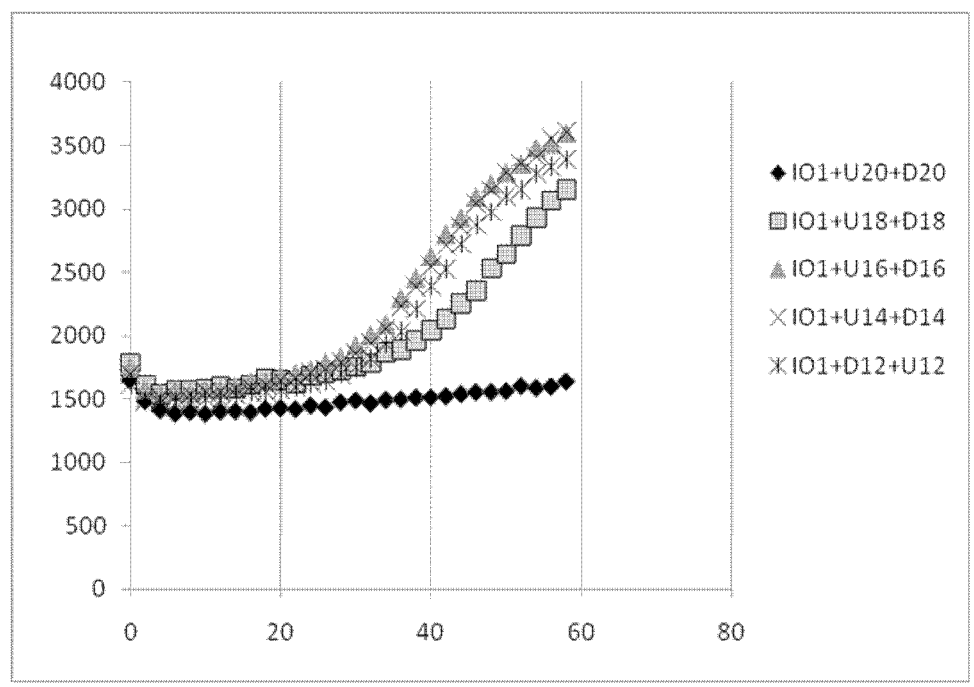
FIG. 8 shows the effect of primer length in a tripartite system.

The results are shown in FIG. 8. Primers of 12, 14 and 16 bases amplified efficiently. The primer set of 18 bases amplified less efficiently and the 20 base primer set did not amplify and therefore would not form artefacts.

Example 4

Figure 9A:
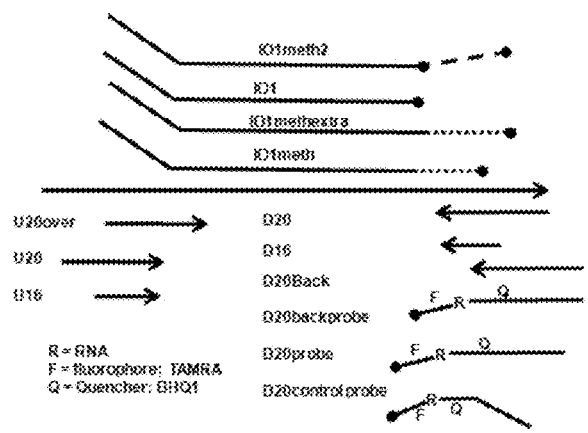
FIG. 9A shows template/primer/oligonucleotide configurations including downstream 2-O-methylated oligonucleotides and probes.
Figure 9B:
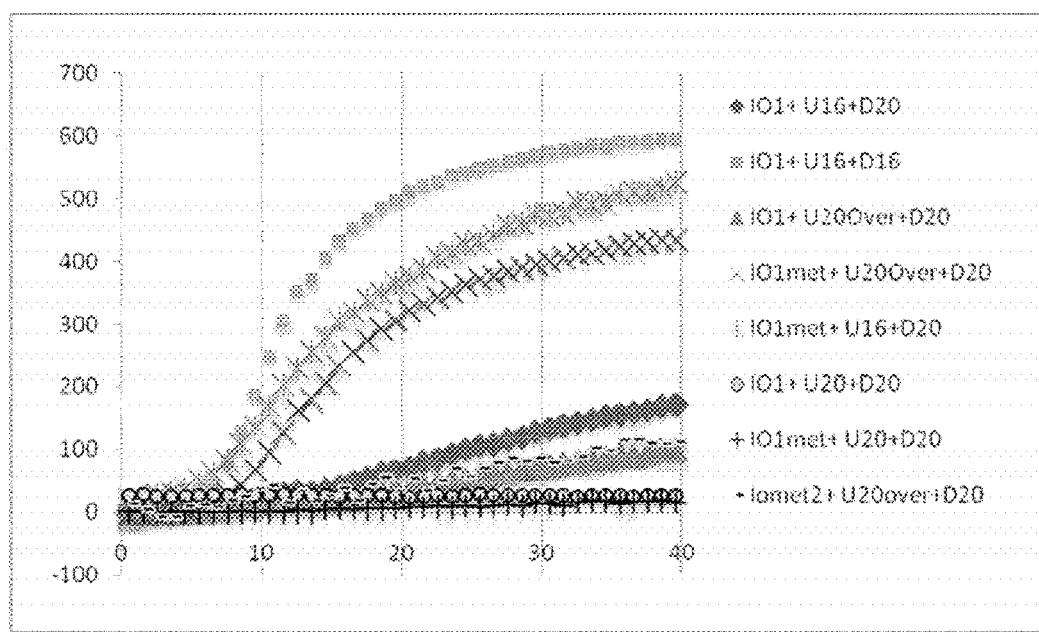
FIG. 9B shows the effect of using a intermediate oligonucleotide having a methylated downstream element.

Artefacts can be Aborgated Using Methylated Downstream Elements in the Intermediate Oligonucleotide The protocol used is the same as that described above unless otherwise stated. Template/oligonucleotide/primer configurations are shown in FIG. 9A. Primers were used at a concentration of 300 nM each. Intermediate oligonucleotide (IO1) was used at 150 nM and template concentration was 10 pM. The signal was produced by Sybr green fluorescence.

In the three primer system longer primers (20BP) are unable to amplify (IO1+U20+D20 and IO1met+U20+D20) since the regions upstream and downstream of the invading intermediate oligonucleotide are too long to separate and allow the primers to bind. Furthermore after the intermediate oligonucleotide binding event is complete and the recombinase depolymerises (falls off the oligonucleotide), the duplex, which is not fully separated tends to close again by branch migration.

If the downstream primer is long and the upstream primer is short then amplification is slow (IO1+U16+D20) but visible. This is because the upstream region is separated when the IO invades allowing the upstream primer to bind but it has to compete with the partially tethered duplex during extension.

If the upstream primer is long but overlaps the intermediate then some slow amplification is also observed with a long downstream primer (IO1+U20over+D20). This is because, although the primer is long the region of the amplified template upstream of the IO remains short (see FIG. 9A).

If the downstream primer is long and a methylated downstream element is incorporated into the intermediate (IO1meth+U16+D20 and IO1meth+U20over+D20) then the amplification rate is increased to that similar to a short downstream primer. This is because the methylated region of the IO branch migrates into the downstream region of the duplex shortening the remaining duplex, separating the duplex strand allowing primer to bind and freeing extension of the upstream primer from competition with a partially tethered template. The methylated element must be cognate and therefore able to branch migrate since IO1Met2+ U20over+D20 does not show accelerated amplification. This is the case even where the upstream primer is long if it overlaps the intermediate (IO1meth+U20over+D20).

Despite the rapid amplification using long primers and the methylated intermediate, if the long upstream primer does not overlap the intermediate then there are is no amplification and no artefacts (IO1meth+U20+D20). It is likely that this is due to the concept that where the upstream region remains intact the amplification must be initiated by the downstream primer. The region downstream of the intermediate tends to be covered in recombinase until the recombinase depolymerises and consequently cannot bind primer until the recombinase has depolymerised by which time the duplex has closed by branch migration. These observations demonstrate that rapid amplification using a methylated intermediate oligonucleotide and long primers is possible and relies on a cognate methylated region of the intermediate. Since the cognate region of the methylated moieties are not substrates for a polymerase, artefacts are not possible.

Example 5

The Three Oligonucleotide System can Amplify from Biologically Derived DNA

The protocol used is the same as that described above unless otherwise stated and the oligonucleotide are as shown in the legend and configured as shown in FIG. 9A. Primers were used at a concentration of 300 nM each. Intermediate oligonucleotide (IO1) was used at 150 nM and template concentration was 1 fM. Template1 with an additional ALU1 sensitive agct sequence immediately upstream of the oligonucleotide was inserted into the plasmid vector PXero-2 by IDT-DNA (San-Diego). The signal was produced by Sybr green fluorescence. Plasmid was cleaved with ALU1 using 0.1 ug of plasmid in 100 ul (1 nM) and digestion for 30 mins at 37° C. with 5 units of ALU1 (New England Biolabs) in NEB buffer 4. The plasmid template was subsequently diluted in water as described in the standard operating procedure.

Amplification of this template1 inserted into the plasmid was compared with that of the synthetic template and also with the plasmid cleaved immediately upstream of the template sequence. As discussed above (example 4), the region of template upstream of the intermediate oligonucleotide needs to be short for efficient amplification. In a biological system the target template is usually part of a long sequence of DNA and the duplex upstream of the intermediate oligonucleotide may be longer than that desired for efficient amplification. This could effect the first cycle of amplification in such systems unless the template is heated prior to amplification rendering the template single stranded. The importance of this issue was assessed using plasmid DNA.

Figure 10:
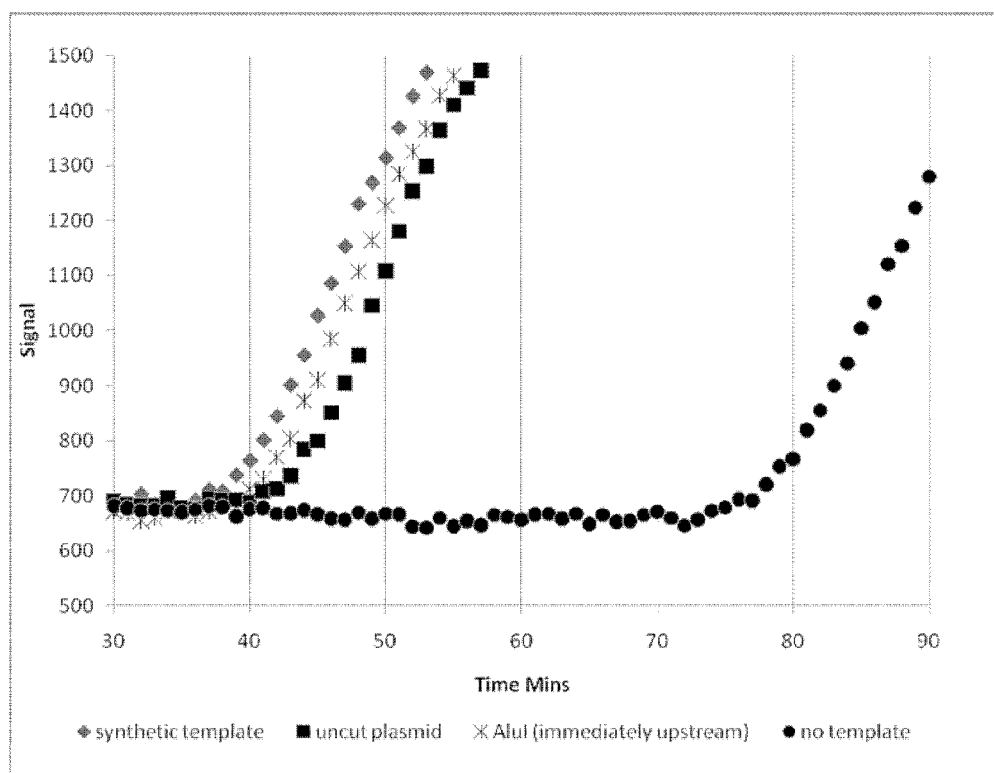
FIG. 10 shows that a tripartite system can amplify from biologically derived DNA.

The results are shown in FIG. 10. There was a delay of several minutes for amplification of the plasmid and a smaller delay where the plasmid was cleaved upstream of the template. It may be that negative super coiling of the plasmid facilitated the first round of amplification however a plasmid cleaved downstream of the template also produced amplification after a similar delay. Alternatively occasional breathing of the duplex may have enabled amplification after a delay Amplification of the no template control was seen but this was after a single molecule of the template would have been detected. It is likely that the methylated portion of IO1 was copied at a very slow rate by the polymerase eventually forming an artefact. There was only a single methylated base between overlap of the primer terminus with the methylated region of the intermediate and the DNA portion of the intermediate which may have enabled eventual read-through in this area. In subsequent experiments the number of bases between the primer and the DNA portion of the intermediate were increased to avoid all artefactual amplification.

Example 6

The Sensitivity of the System Using a Methylate Intermediate can be at the Level of a Single Molecule The protocol used is the same as that described above unless otherwise stated. The oligonucleotides used were U20over, template1, IO1methextra and D20back. This configuration was used to avoid any artefactual amplification events since the IOmethextra comprises additional 2'-methylated RNA bases compared with IO1meth decreasing further the opportunity of the downstream primer to copy through the additional 2'-methylated bases to the point that this becomes implausible. The oligonucleotide configuration is shown in FIG. 9A. The signal was produced by Sybr green fluorescence.

Figure 11A:
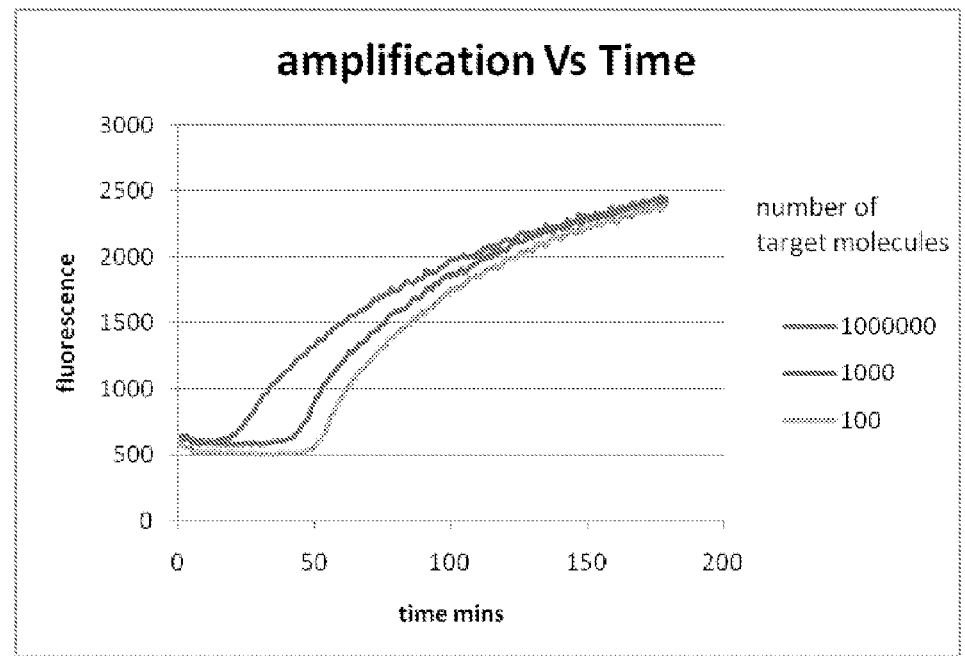
FIG. 11A shows the result of amplification with a tripartite system using 75 nM of downstream methylated intermediate oligonucelotide.
Figure 11B:
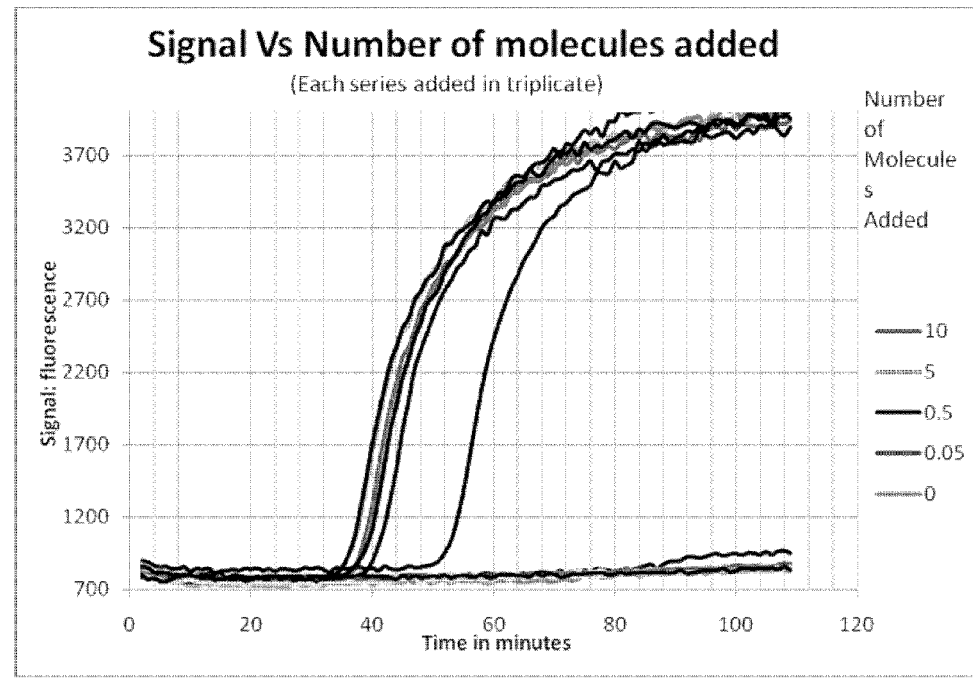
FIG. 11B shows that the sensitivity of the tripartite system using a downstream methylate intermediate can be at the level of a single molecule.

The results are shown in FIGS. 11A and 11B. In FIG. 11A the intermediate was used at 75 nM whereas in FIG. 11B the intermediate was used at 150 nM. Primer concentrations were 200 nM. In FIG. 11A 1 million, 1000 and one hundred molecules were added. In FIG. 11B the assay comprised the addition of 10, 5, 0.5, 0.05 and 0 molecules of template 1 to each test such that 0.5 molecules had a ½ chance of containing a single molecule. Three samples of each concentration were prepared and the results are shown. All samples with 10 and five molecules amplified. One of the three samples that had a ½ chance of containing a molecule amplified (the sample with amplification delayed). No other samples amplified.

Example 7

Crowding Agents can Improve the Kinetics of the System

The protocol used is the same as that described in Example 1 unless otherwise stated. The oligonucleotides are as shown in the legend and configured as shown in FIG. 9A. Primers were U16 and D16 used at a concentration of 200 nM each. Intermediate oligonucleotide (IO1) concentrations were 150 nM and template-1 concentration was 100 pM. The signal was produced by Sybr green fluorescence.

Figure 12:
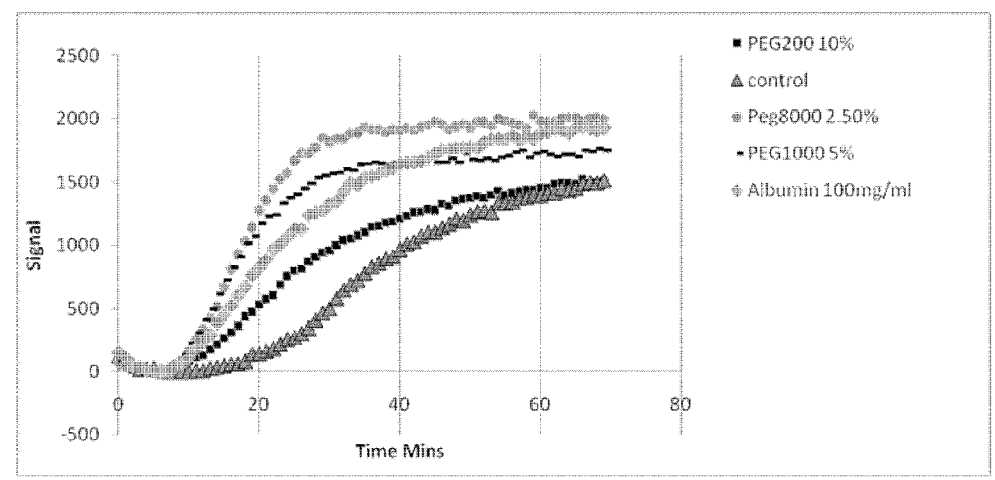
FIG. 12 shows the use of crowding agents in tripartite system.

The results are shown in FIG. 12. The system was viable without crowding agents but amplified more efficiently in the presence of different types of PEG or albumin as previously reported (Reddy M K et. Al. Methods Enzymol. 1995; 262:466-76; Lavery P et. Al. JBC 1992, 26713, 9307-9314; WO2008/035205).

Example 8

Figure 13:
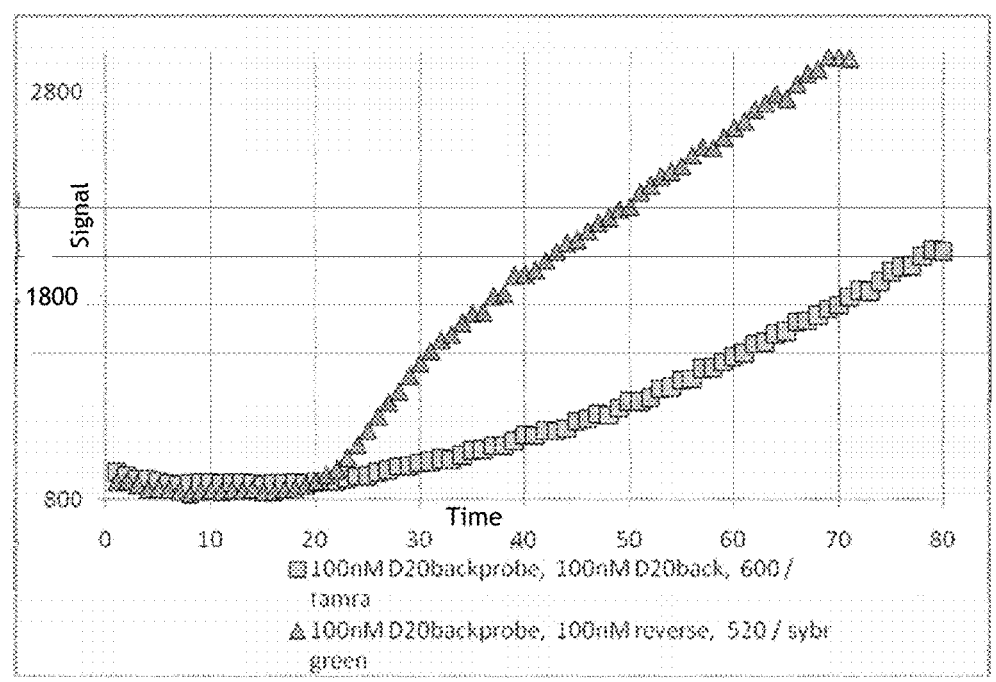
FIG. 13 shows amplification in a tripartite system interrogated by probes.

The Amplification can be Interrogated by Probes Instead of Sybr Green in Order to Multiplex the Reaction or for the Purpose of Incorporation of Positive and Negative Controls The protocol used is the same as that described in Example 1 unless otherwise stated. The oligonucleotides used were U20over (200 nM), template1, IO1meth (75 nM), and a mixture of D20 and D20probe at the concentrations of 100 nM each. The concentration of template was 100 fM. The oligonucleotide configuration is shown in FIG. 9A. RNASEH from *T. kodakaraensis* was added at a final concentration of 1 nM together with the other components. The system was excited and read at 480/520 nm to assess amplification or 540/600 nm to interrogate probe cleavage. The probe was incorporated as part of the downstream primer system. The primer comprised a template cognate region, an RNA base and a blocked non cognate region at its 3' terminus. The RNA base was cleaved by RNASEHII when the primer bound to template allowing the primer to extend. Since the primer comprised a quencher and fluorophore either side of the RNA base, they became separated on cleavage of the RNA base producing a signal. FIG. 13 shows both the signal produced by Sybr green and the signal induced by the probe.

A probe primer designed to assess the presence of a template could be used together with an additional probe primer incorporating an alternative fluorophore. Such a system can be configured for the purpose of positive and negative controls where a control template is added at a known concentration as part of the system. Alternatively, and in the event that the system could induce artefactual amplification, then a probe primer that induces earlier artefactual amplification could be added and where a signal is produced by the amplification of such a probe then the test would be terminated. This is exemplified by the use of D20control probe and D20back in FIG. 9a where D20control will induce earlier artifactual amplification due to its closer proximity to the DNA bases of the intermediate.

| Sequences | | |
|---|---|---|
| U40 | GTTACGATTGTCCTAATGGAGAGTGAGTTGTGATGATGTC | (SEQ ID NO: 1) |
| U35 | GATTGTCCTAATGGAGAGTGAGTTGTGATGATGTC | (SEQ ID NO: 2) |
| U32 | TGTCCTAATGGAGAGTGAGTTGTGATGATGTC | (SEQ ID NO: 3) |
| U23-overlap | GAGTTGTGATGATGTC ATTCGCA | (SEQ ID NO: 4) |
| U23 | CGAGAGTGAGTTGTGATGATGTC | (SEQ ID NO: 5) |
| U20 | GAGTGAGTTGTGATGATGTC | (SEQ ID NO: 6) |
| U18 | GTGAGTTGTGATGATGTC | (SEQ ID NO: 7) |
| U15 | AGTTGTGATGATGTC | (SEQ ID NO: 8) |
| U12 | TGTGATGATGTC | (SEQ ID NO: 9) |
| D40 | TCTGGCATGTTACAAGGTCAAGATGAACCAACCACTTATA | (SEQ ID NO: 10) |
| D35 | CATGTTACAAGGTCAAGATGAACCAACCACTTATA | (SEQ ID NO: 11) |
| D32 | GTTACAAGGTCAAGATGAACCAACCACTTATA | (SEQ ID NO: 12) |
| D23 | TCAAGATGAACCAACCACTTATA | (SEQ ID NO: 13) |
| D20 | AGATGAACCAACCACTTATA | (SEQ ID NO: 14) |
| D18 | ATGAACCAACCACTTATA | (SEQ ID NO: 15) |
| D16 | GAACCAACCACTTATA | (SEQ ID NO: 16) |
| D14 | ACCAACCACTTATA | (SEQ ID NO: 17) |
| D12 | CAACCACTTATA | (SEQ ID NO: 18) |
| D20back | GGTCAAGATGAACCAACCAC | (SEQ ID NO: 19) |

X = blocked base comprimising 3' amino-6carbon-spacer
X = 2'-O-methyl RNA
X = RNA base
TQ is a T attached to a BHQ2
TF is a T attached to Tetramethylrhodamine (TAMRA)

| | | |
|---|---|---|
| I01 | TGAGCATAGACGGCATTCGCAGATCCAGTCAGCAGTTCTT CTCACTCTTCA<u>A</u> | (SEQ ID NO: 20) |
| I02 | GAGGCTAAGGAATACACGCAAAGGCGGCTTGGTGTTCTTT CAGTTCTTCA<u>A</u> | SEQ (ID NO: 21) |
| I01met | TGAGCATAGACGGCATTCGCAGATCCAGTCAGCAGTTCTT CTCACTCTTCAA*GTATA*G | (SEQ ID NO: 22) |
| I01met extra | TGAGCATAGACGGCATTCGCAGATCCAGTCAGCAGTTCTT CTCACTCTTCAA*GTATAAGTGG*<u>A</u> | (SEQ ID NO: 23) |
| I01met2 | TGAGCATAGACGGCATTCGCAGATCCAGTCAGCAGTTCTT CTCACTCTTCAA*TTCTA*G | (SEQ ID NO: 24) |
| Template A | GTTACGATTGTCCTAATGGAGAGTGAGTTGTGATGATGTC CTGTATAAGTGGTTGGTTCATCTTGACCTTGTAACATGCC AG | (SEQ ID NO: 25) |
| Template 1 | GTTACGATTGTCCTAATGGAGAGTGAGTTGTGATGATGTC ATTCGCAGATCCAGTCAGCAGTTCTTCTCACTCTTCAAGT ATAAGTGGTTGGTTCATCTTGACCTTGTAACATGCCAG | (SEQ ID NO: 26) |
| Template 2 | GTTACGATTGTCCTAATGGAGAGTGAGTTGTGATGATGTC ACAGCCAAAGGCGGCTTGGTGTTCTTTCAGTTCTTCAAGT ATAAGTGGTTGGTTCATCTTGACCTTGTAACATGCCAG | (SEQ ID NO: 27) |
| D20probe | AGATGAACCAACCAC(TQ)TAT<u>A</u>TTT(TF)TTT | (SEQ ID NO: 28) |
| D20probe2 | T(TF)TTTT<u>T</u>AGA(TQ)GAACCAACCACTTATA | (SEQ ID NO: 29) |

The invention claimed is:

1. A kit for isothermal amplification of a double-stranded nucleic acid target molecule, the kit comprising:
   (i) a recombinase;
   (ii) an upstream nucleic acid primer and a downstream nucleic acid primer that do not bind the double-stranded nucleic acid target molecule, are not substrates for the recombinase, and do not amplify the target molecule independently of the recombinase, wherein each of said upstream and downstream nucleic acid primers comprises a single-stranded DNA molecule of less than 25 nucleotides, wherein at least a portion of each nucleic acid primer is complementary to a sequence of the target molecule; and
   (iii) an oligonucleotide comprising a single-stranded DNA molecule of at least 30 nucleotides, at least 24 of said nucleotides of said oligonucleotide are complementary to the target molecule in a region between upstream and downstream nucleic acid primer binding sites, and at least a portion of the oligonucleotide is substrate for the recombinase.

2. The kit of claim 1, wherein the oligonucleotide has a non-extendable 3' terminus.

3. The kit of claim 1, wherein the recombinase is UvsX.

4. The kit of claim 3, further comprising at least one recombinase accessory protein.

5. The kit of claim 1, wherein each of the upstream and downstream nucleic acid primers comprises a single-stranded DNA molecule of 12 to 24 nucleotides.

6. The kit of claim 5, wherein the at least one recombinase accessory protein is gp32.

7. The kit of claim 5, wherein the at least one recombinase accessory protein is UvsY.

8. The kit of claim 1, wherein the oligonucleotide comprises a downstream element at its 3' terminus which is complementary to the target molecule and which is not a polymerase substrate.

9. The kit of claim 1 further comprising a strand displacing polymerase.

10. The kit of claim 1, wherein the upstream nucleic acid primer comprises a sequence which overlaps with the oligonucleotide.

11. The kit of claim 10, wherein 5 to 10 nucleotides of a terminus of the upstream nucleic acid primer overlap with the oligonucleotide.

12. The kit of claim 8, wherein the downstream nucleic acid primer comprises a sequence which is complementary to a sequence of the downstream element of the oligonucleotide.

13. The kit of claim 1, wherein 24 to 63 nucleotides of the oligonucleotide is complementary to the target molecule.

14. The kit of claim 1, wherein each of the upstream and downstream nucleic acid primers comprises a single-stranded DNA molecule of 12 to 25 nucleotides.

15. The kit of claim 14, wherein each of the upstream and downstream nucleic acid primers comprises a single-stranded DNA molecule of 15 to 23 nucleotides.

* * * * *

SEQUENCE LISTING

<160> NUMBER OF SEQ ID NOS: 30

<210> SEQ ID NO 1
<211> LENGTH: 40
<212> TYPE: DNA
<213> ORGANISM: Artificial
<220> FEATURE:
<223> OTHER INFORMATION: U40 primer

<400> SEQUENCE: 1
gttacgattg tcctaatgga gagtgagttg tgatgatgtc          40

<210> SEQ ID NO 2
<211> LENGTH: 35
<212> TYPE: DNA
<213> ORGANISM: Artificial
<220> FEATURE:
<223> OTHER INFORMATION: U35 primer

<400> SEQUENCE: 2
gattgtccta atggagagtg agttgtgatg atgtc          35

<210> SEQ ID NO 3
<211> LENGTH: 32
<212> TYPE: DNA
<213> ORGANISM: Artificial
<220> FEATURE:
<223> OTHER INFORMATION: U32 primer

<400> SEQUENCE: 3
tgtcctaatg gagagtgagt tgtgatgatg tc          32

<210> SEQ ID NO 4
<211> LENGTH: 23
<212> TYPE: DNA
<213> ORGANISM: Artificial
<220> FEATURE:
<223> OTHER INFORMATION: U23-overlap primer

<400> SEQUENCE: 4
gagttgtgat gatgtcattc gca          23

<210> SEQ ID NO 5
<211> LENGTH: 23
<212> TYPE: DNA
<213> ORGANISM: Artificial
<220> FEATURE:
<223> OTHER INFORMATION: U23 primer

<400> SEQUENCE: 5
cgagagtgag ttgtgatgat gtc          23

<210> SEQ ID NO 6
<211> LENGTH: 20
<212> TYPE: DNA
<213> ORGANISM: Artificial
<220> FEATURE:
<223> OTHER INFORMATION: U20 primer

<400> SEQUENCE: 6
gagtgagttg tgatgatgtc          20

<210> SEQ ID NO 7
<211> LENGTH: 18
<212> TYPE: DNA
<213> ORGANISM: Artificial
<220> FEATURE:
<223> OTHER INFORMATION: U18 primer

<400> SEQUENCE: 7
gtgagttgtg atgatgtc          18

<210> SEQ ID NO 8

```
<211> LENGTH: 15
<212> TYPE: DNA
<213> ORGANISM: Artificial
<220> FEATURE:
<223> OTHER INFORMATION: U15 primer

<400> SEQUENCE: 8
agttgtgatg atgtc                                                    15

<210> SEQ ID NO 9
<211> LENGTH: 12
<212> TYPE: DNA
<213> ORGANISM: Artificial
<220> FEATURE:
<223> OTHER INFORMATION: U12 primer

<400> SEQUENCE: 9
tgtgatgatg tc                                                       12

<210> SEQ ID NO 10
<211> LENGTH: 40
<212> TYPE: DNA
<213> ORGANISM: Artificial
<220> FEATURE:
<223> OTHER INFORMATION: D40 primer

<400> SEQUENCE: 10
tctggcatgt tacaaggtca agatgaacca accacttata                         40

<210> SEQ ID NO 11
<211> LENGTH: 35
<212> TYPE: DNA
<213> ORGANISM: Artificial
<220> FEATURE:
<223> OTHER INFORMATION: D35 primer

<400> SEQUENCE: 11
catgttacaa ggtcaagatg aaccaaccac ttata                              35

<210> SEQ ID NO 12
<211> LENGTH: 32
<212> TYPE: DNA
<213> ORGANISM: Artificial
<220> FEATURE:
<223> OTHER INFORMATION: D32 primer

<400> SEQUENCE: 12
gttacaaggt caagatgaac caaccactta ta                                 32

<210> SEQ ID NO 13
<211> LENGTH: 23
<212> TYPE: DNA
<213> ORGANISM: Artificial
<220> FEATURE:
<223> OTHER INFORMATION: D23 primer

<400> SEQUENCE: 13
tcaagatgaa ccaaccactt ata                                           23

<210> SEQ ID NO 14
<211> LENGTH: 20
<212> TYPE: DNA
<213> ORGANISM: Artificial
<220> FEATURE:
<223> OTHER INFORMATION: D20 primer

<400> SEQUENCE: 14
```

```
agatgaacca accacttata                                              20

<210> SEQ ID NO 15
<211> LENGTH: 18
<212> TYPE: DNA
<213> ORGANISM: Artificial
<220> FEATURE:
<223> OTHER INFORMATION: D18 primer

<400> SEQUENCE: 15
atgaaccaac cacttata                                                18

<210> SEQ ID NO 16
<211> LENGTH: 16
<212> TYPE: DNA
<213> ORGANISM: Artificial
<220> FEATURE:
<223> OTHER INFORMATION: D16 primer

<400> SEQUENCE: 16
gaaccaacca cttata                                                  16

<210> SEQ ID NO 17
<211> LENGTH: 14
<212> TYPE: DNA
<213> ORGANISM: Artificial
<220> FEATURE:
<223> OTHER INFORMATION: D14 primer

<400> SEQUENCE: 17
accaaccact tata                                                    14

<210> SEQ ID NO 18
<211> LENGTH: 12
<212> TYPE: DNA
<213> ORGANISM: Artificial
<220> FEATURE:
<223> OTHER INFORMATION: D12 primer

<400> SEQUENCE: 18
caaccactta ta                                                      12

<210> SEQ ID NO 19
<211> LENGTH: 20
<212> TYPE: DNA
<213> ORGANISM: Artificial
<220> FEATURE:
<223> OTHER INFORMATION: D20back primer

<400> SEQUENCE: 19
ggtcaagatg aaccaaccac                                              20

<210> SEQ ID NO 20
<211> LENGTH: 52
<212> TYPE: DNA
<213> ORGANISM: Artificial
<220> FEATURE:
<223> OTHER INFORMATION: oligonucleotide IO1
<220> FEATURE:
<221> NAME/KEY: modified_base
<222> LOCATION: (52)..(52)
<223> OTHER INFORMATION: blocked base comprising 3' amino-6carbon-spacer

<400> SEQUENCE: 20
tgagcataga cggcattcgc agatccagtc agcagttctt ctcactcttc aa          52
```

```
<210> SEQ ID NO 21
<211> LENGTH: 51
<212> TYPE: DNA
<213> ORGANISM: Artificial
<220> FEATURE:
<223> OTHER INFORMATION: oligonucleotide IO2
<220> FEATURE:
<221> NAME/KEY: modified_base
<222> LOCATION: (51)..(51)
<223> OTHER INFORMATION: 3' amino-6carbon-spacer
<220> FEATURE:
<221> NAME/KEY: modified_base
<222> LOCATION: (51)..(51)
<223> OTHER INFORMATION: blocked base comprising 3' amino-6carbon-spacer

<400> SEQUENCE: 21
gaggctaagg aatacacgca aaggcggctt ggtgttcttt cagttcttca a          51

<210> SEQ ID NO 22
<211> LENGTH: 58
<212> TYPE: DNA
<213> ORGANISM: Artificial
<220> FEATURE:
<223> OTHER INFORMATION: oligonucleotide IO1met
<220> FEATURE:
<221> NAME/KEY: misc_RNA
<222> LOCATION: (53)..(57)
<223> OTHER INFORMATION: 2'-O-methyl RNA
<220> FEATURE:
<221> NAME/KEY: modified_base
<222> LOCATION: (58)..(58)
<223> OTHER INFORMATION: blocked base comprising 3' amino-6carbon-spacer

<400> SEQUENCE: 22
tgagcataga cggcattcgc agatccagtc agcagttctt ctcactcttc aagtatag    58

<210> SEQ ID NO 23
<211> LENGTH: 63
<212> TYPE: DNA
<213> ORGANISM: Artificial
<220> FEATURE:
<223> OTHER INFORMATION: oligonucleotide IO1met extra
<220> FEATURE:
<221> NAME/KEY: misc_RNA
<222> LOCATION: (53)..(62)
<223> OTHER INFORMATION: 2'-O-methyl RNA
<220> FEATURE:
<221> NAME/KEY: modified_base
<222> LOCATION: (63)..(63)
<223> OTHER INFORMATION: blocked base comprising 3' amino-6carbon-spacer

<400> SEQUENCE: 23
tgagcataga cggcattcgc agatccagtc agcagttctt ctcactcttc aagtataagt  60
gga                                                              63

<210> SEQ ID NO 24
<211> LENGTH: 58
<212> TYPE: DNA
<213> ORGANISM: Artificial
<220> FEATURE:
<223> OTHER INFORMATION: oligonucleotide IO1met2
<220> FEATURE:
<221> NAME/KEY: misc_RNA
<222> LOCATION: (53)..(57)
<223> OTHER INFORMATION: 2'-O-methyl RNA
<220> FEATURE:
<221> NAME/KEY: modified_base
<222> LOCATION: (58)..(58)
<223> OTHER INFORMATION: blocked base comprising 3' amino-6carbon-spacer

<400> SEQUENCE: 24
```
tgagcataga cggcattcgc agatccagtc agcagttctt ctcactcttc aattctag        58

<210> SEQ ID NO 25
<211> LENGTH: 82
<212> TYPE: DNA
<213> ORGANISM: Artificial
<220> FEATURE:
<223> OTHER INFORMATION: Template A

<400> SEQUENCE: 25
gttacgattg tcctaatgga gagtgagttg tgatgatgtc ctgtataagt ggttggttca        60
tcttgacctt gtaacatgcc ag        82

<210> SEQ ID NO 26
<211> LENGTH: 118
<212> TYPE: DNA
<213> ORGANISM: Artificial
<220> FEATURE:
<223> OTHER INFORMATION: Template 1

<400> SEQUENCE: 26
gttacgattg tcctaatgga gagtgagttg tgatgatgtc attcgcagat ccagtcagca        60
gttcttctca ctcttcaagt ataagtggtt ggttcatctt gaccttgtaa catgccag        118

<210> SEQ ID NO 27
<211> LENGTH: 118
<212> TYPE: DNA
<213> ORGANISM: Artificial
<220> FEATURE:
<223> OTHER INFORMATION: Template 2

<400> SEQUENCE: 27
gttacgattg tcctaatgga gagtgagttg tgatgatgtc acacgcaaag gcggcttggt        60
gttctttcag ttcttcaagt ataagtggtt ggttcatctt gaccttgtaa catgccag        118

<210> SEQ ID NO 28
<211> LENGTH: 27
<212> TYPE: DNA
<213> ORGANISM: Artificial
<220> FEATURE:
<223> OTHER INFORMATION: D20probe
<220> FEATURE:
<221> NAME/KEY: modified_base
<222> LOCATION: (16)..(16)
<223> OTHER INFORMATION: BHQ2-modified base
<220> FEATURE:
<221> NAME/KEY: misc_RNA
<222> LOCATION: (20)..(20)
<220> FEATURE:
<221> NAME/KEY: modified_base
<222> LOCATION: (24)..(24)
<223> OTHER INFORMATION: Tetramethylrhodamine (TAMRA) - modified base

<400> SEQUENCE: 28
agatgaacca accacttata ttttttt        27

<210> SEQ ID NO 29
<211> LENGTH: 27
<212> TYPE: DNA
<213> ORGANISM: Artificial
<220> FEATURE:
<223> OTHER INFORMATION: D20probe2
<220> FEATURE:
<221> NAME/KEY: modified_base
<222> LOCATION: (2)..(2)
<223> OTHER INFORMATION: Tetramethylrhodamine (TAMRA) - modified base

```
<220> FEATURE:
<221> NAME/KEY: misc_RNA
<222> LOCATION: (7)..(7)
<220> FEATURE:
<221> NAME/KEY: modified_base
<222> LOCATION: (11)..(11)
<223> OTHER INFORMATION: BHQ2-modified base

<400> SEQUENCE: 29
tttttttaga tgaaccaacc acttata                                      27

<210> SEQ ID NO 30
<211> LENGTH: 4
<212> TYPE: DNA
<213> ORGANISM: Artificial
<220> FEATURE:
<223> OTHER INFORMATION: ALU1 sensitive sequence

<400> SEQUENCE: 30 agct                                                                4
```